United States Patent
Sato et al.

(10) Patent No.: US 9,988,170 B2
(45) Date of Patent: Jun. 5, 2018

(54) METHOD OF STERILIZING PREFORM AND METHOD OF STERILIZING CONTAINER MADE OF RESIN

(71) Applicant: Dai Nippon Printing Co., Ltd., Tokyo (JP)

(72) Inventors: Yoshinori Sato, Tokyo (JP); Hirotaka Tsuchiya, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 0 days. days.

(21) Appl. No.: 15/329,328

(22) PCT Filed: Sep. 18, 2015

(86) PCT No.: PCT/JP2015/076723
§ 371 (c)(1),
(2) Date: Jan. 26, 2017

(87) PCT Pub. No.: WO2016/047607
PCT Pub. Date: Mar. 31, 2016

(65) Prior Publication Data
US 2017/0217617 A1      Aug. 3, 2017

(30) Foreign Application Priority Data

Sep. 25, 2014 (JP) .................................. 2014-194670
Sep. 25, 2014 (JP) .................................. 2014-194671

(51) Int. Cl.
*A61L 2/14* (2006.01)
*A61L 2/00* (2006.01)
(Continued)

(52) U.S. Cl.
CPC .............. *B65B 55/10* (2013.01); *A61L 2/208* (2013.01); *A61L 2/22* (2013.01); *B65B 3/04* (2013.01);
(Continued)

(58) Field of Classification Search
CPC ... A61L 2/14; A61L 2/22; A61L 2/208; B65B 55/10
(Continued)

(56) References Cited

U.S. PATENT DOCUMENTS 4,511,538 A    4/1985 Buchner et al.
6,562,281 B1    5/2003 Marchau et al.
(Continued)

FOREIGN PATENT DOCUMENTS

JP    58-112930 A    7/1983
JP    H03-224469 A    10/1991
(Continued)

OTHER PUBLICATIONS

English Translation of Japanese Document No. JP H09-99922 A by the European Patent Office espacenet.com: Yamamoto Katsuharu; Method and Device for Sterilization of Food Container; Apr. 15, 1997 (Year: 1997).*

(Continued)

*Primary Examiner* — Kevin Joyner
(74) *Attorney, Agent, or Firm* — Burr & Brown, PLLC

(57) ABSTRACT

A sterilization process is performed on a preform or container made of resin after a corona discharge treatment is performed on an inner surface of the preform or container, the corona discharge treatment including applying a voltage produced in a corona discharge to an electrode that passes through an opening part of the preform or container, an insertion step of inserting the electrode to which the voltage is applied into the preform or container through the opening part, and a bottom part treatment step of treating an inner surface of a bottom part of the preform or container by bringing the electrode close to the bottom part until the corona discharge from the electrode changes discharge mode, and the sterilization process including a hydrogen (Continued)

peroxide supplying step of blasting a mist or gas of hydrogen peroxide solution or a mixture thereof to the preform or container.

20 Claims, 25 Drawing Sheets

(51) Int. Cl.
*B65B 55/10* (2006.01)
*A61L 2/22* (2006.01)
*A61L 2/20* (2006.01)
*B65B 39/00* (2006.01)
*B65B 3/04* (2006.01)
*B65B 7/28* (2006.01)

(52) U.S. Cl.
CPC ............ *B65B 7/2835* (2013.01); *B65B 39/00* (2013.01); *A61L 2202/23* (2013.01)

(58) Field of Classification Search
USPC .......................................................... 422/28
See application file for complete search history.

(56) References Cited

U.S. PATENT DOCUMENTS

| 6,919,043 B2 | 7/2005 | Hayakawa et al. |
| 8,092,757 B2 | 1/2012 | Adriansens et al. |

FOREIGN PATENT DOCUMENTS

| JP | H09-99922 A | 4/1997 |
| JP | 2001-039414 A | 2/2001 |
| JP | 2003-034314 A | 2/2003 |
| JP | 2006-036341 A | 2/2006 |
| JP | 3903411 B | 4/2007 |
| JP | 2008-546605 A | 12/2008 |

OTHER PUBLICATIONS

International Search Report (With English Translation) and Written Opinion, International Application No. PCT/JP2015/076723, dated (6 pages).

* cited by examiner

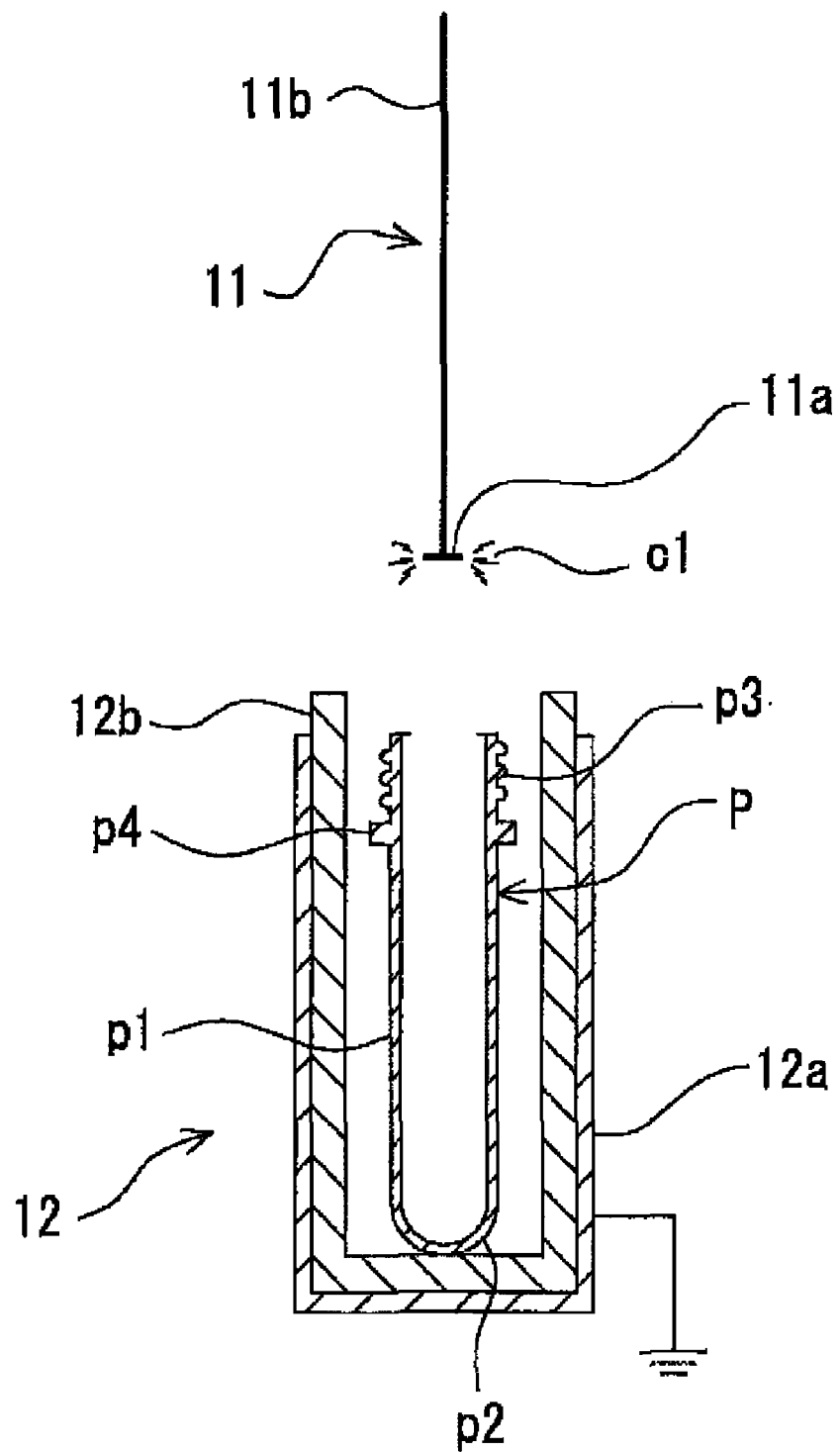

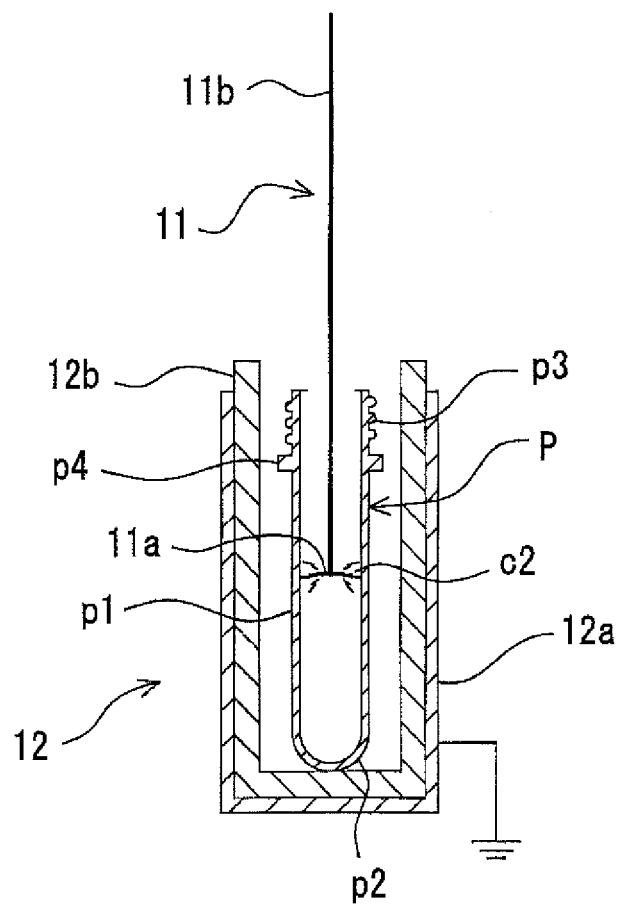

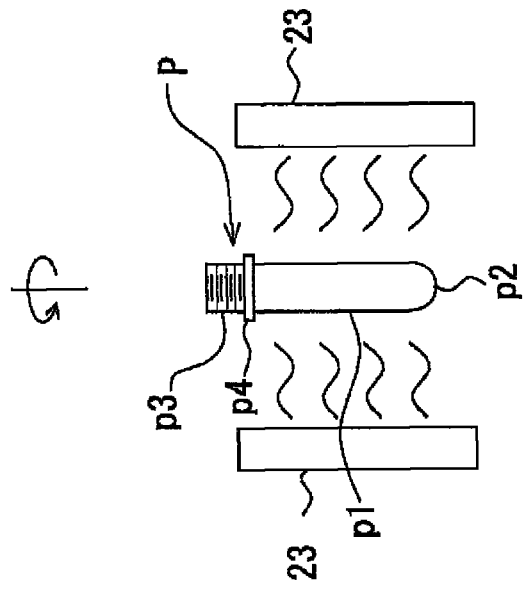
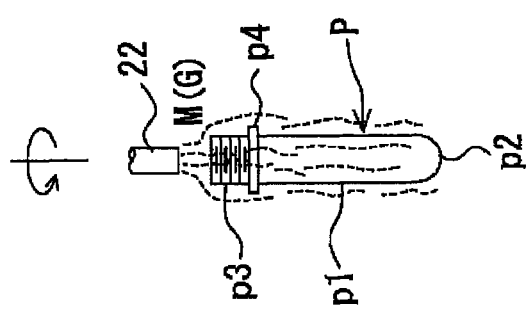
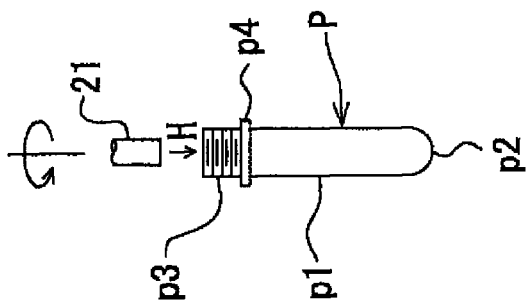

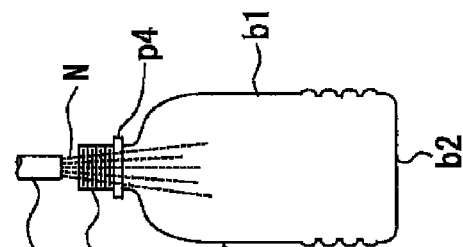
FIG.8(D)
CONTAINER MOLDING
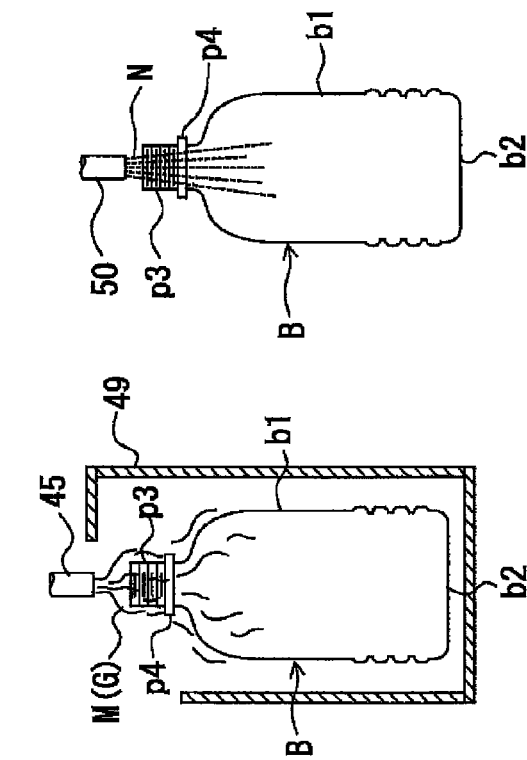
FIG.8(E)
CONTAINER PRELIMINARY HEATING
FIG.8(F)
CONTAINER HYDROGEN PEROXIDE SUPPLY
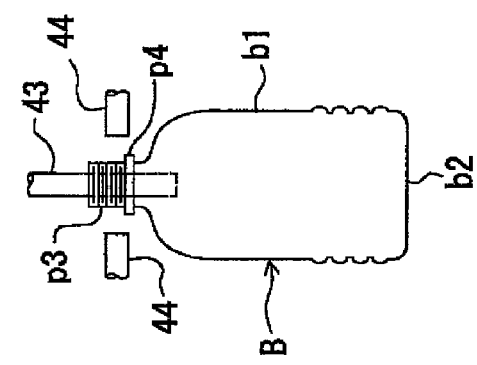
FIG.8(G1)
AIR RINSING
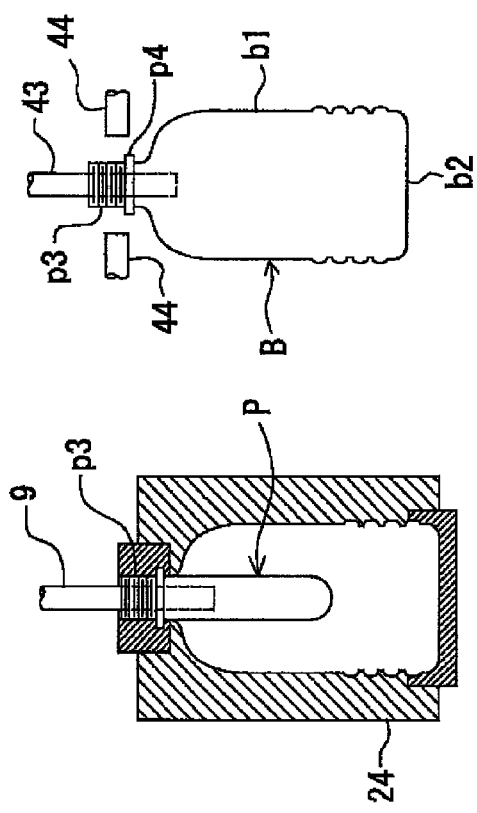

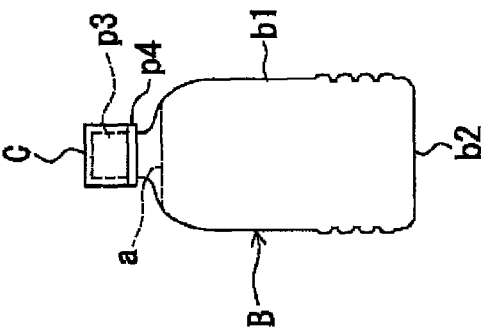
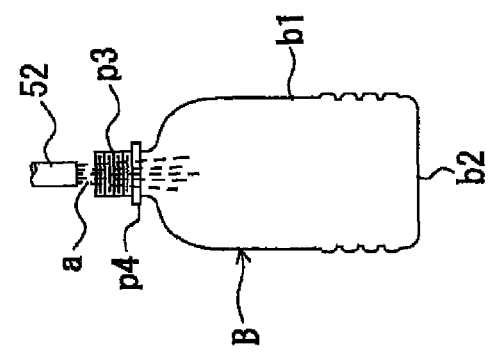
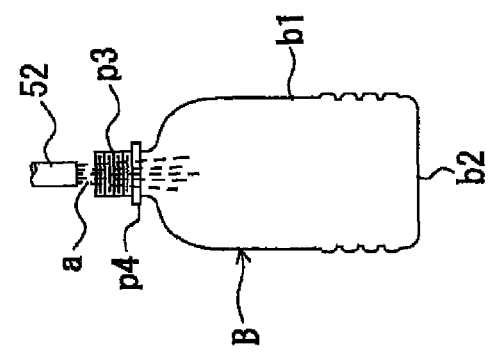
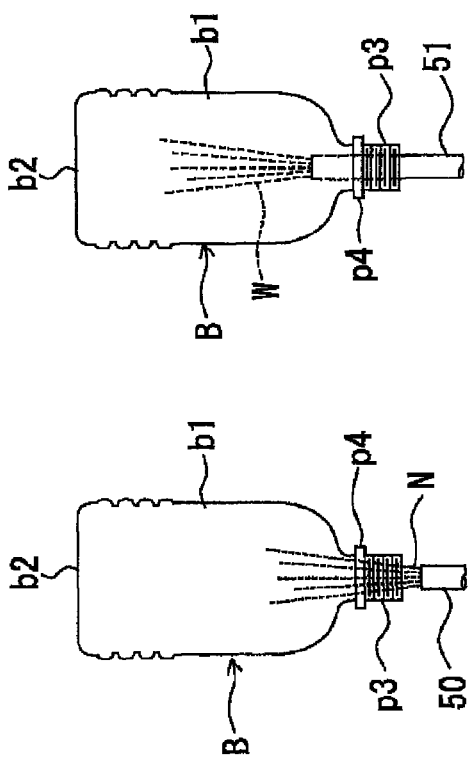

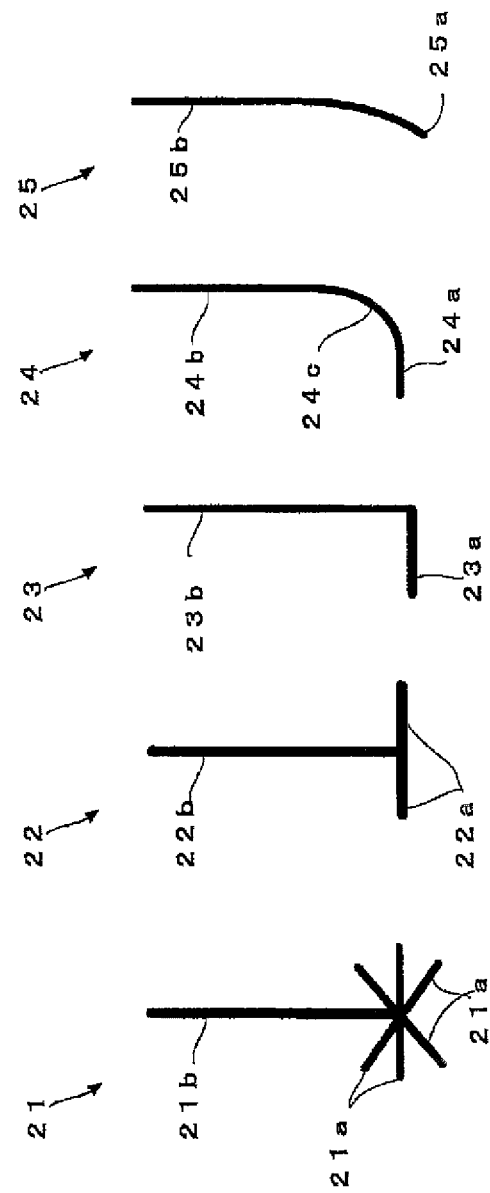

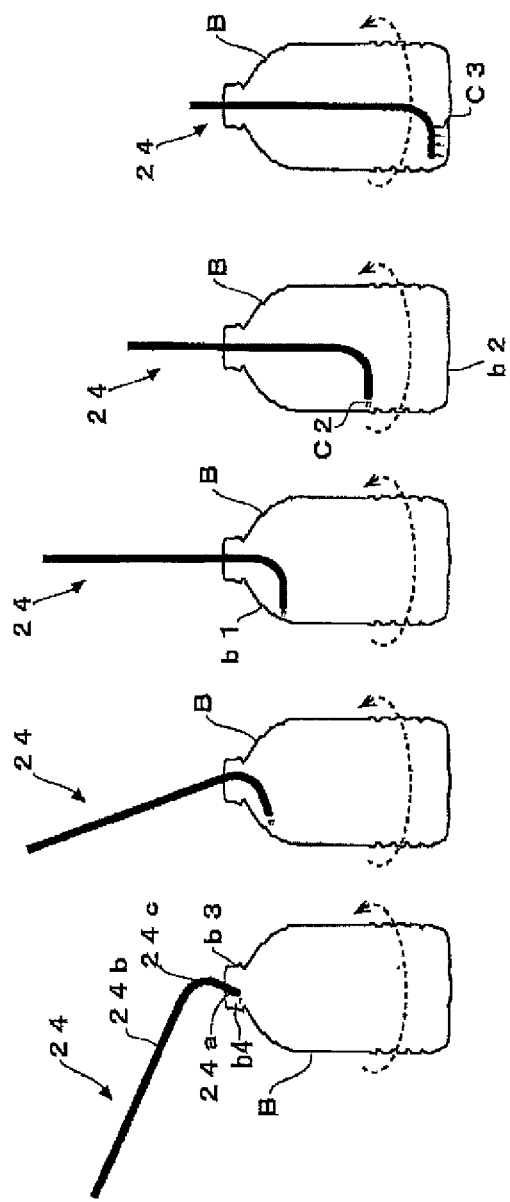

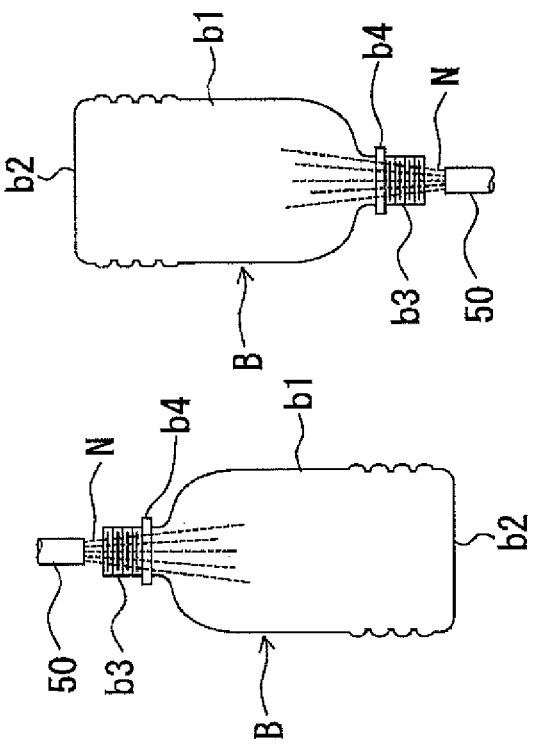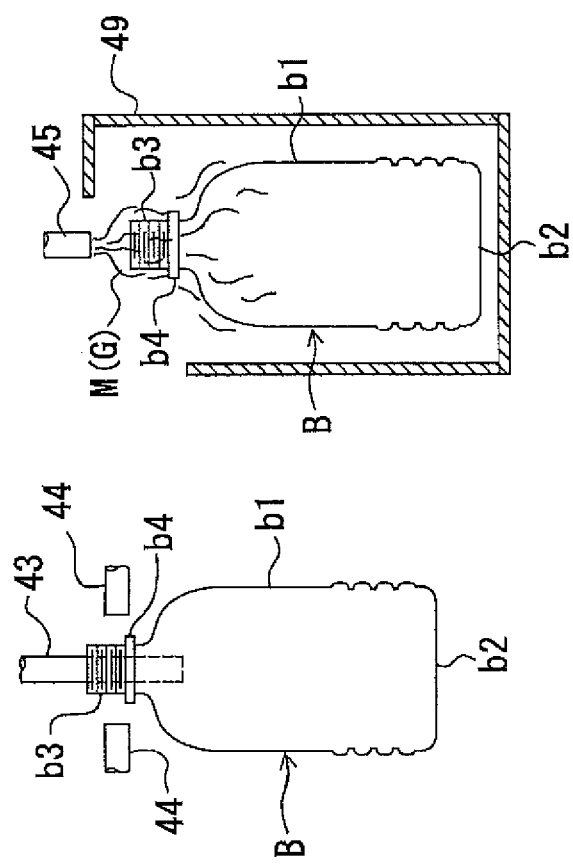

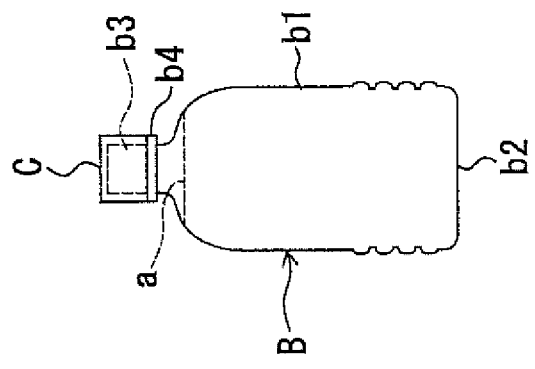
FIG.21(D) WATER RINSING
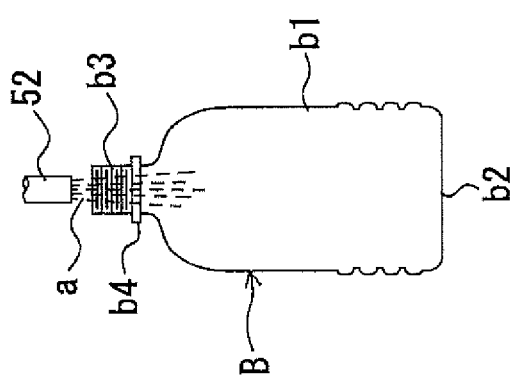
FIG.21(E) CONTENT FILLING
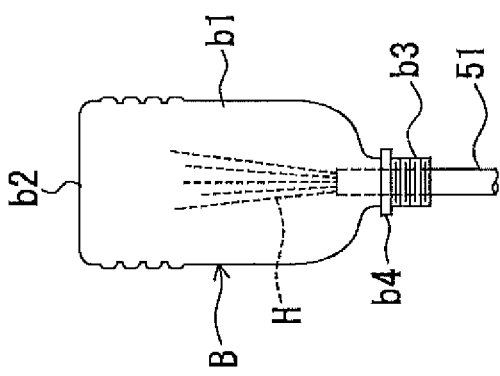
FIG.21(F) SEALING under US 9,988,170 B2

METHOD OF STERILIZING PREFORM AND METHOD OF STERILIZING CONTAINER MADE OF RESIN

TECHNICAL FIELD

The present invention relates to a method of sterilizing a preform and a method of sterilizing a container made of resin.

BACKGROUND ART

According to prior art, an aseptic package is produced by sterilizing a preform made of polyethylene terephthalate (PET) by blasting a sterilizer such as hydrogen peroxide to the preform, heating the preform to a molding temperature, molding the preform into a bottle in a blow molding machine, filling the bottle with a drink, and then putting a cap on the bottle (see Patent Documents 1 and 2, for example).

If a container made of resin is filled with a sterilized content, such as a soup or a drink, the container also needs to be sterilized in advance.

According to prior art, sterilization of the container is performed by blasting a mist or gas of a sterilizer such as hydrogen peroxide or a mixture thereof to the surface of the container (see Patent Documents 3 to 5, for example).

PRIOR ART DOCUMENT

Patent Document

Patent Document 1: Japanese Patent Laid-Open No. 2008-546605
Patent Document 2: Japanese Patent No. 3903411
Patent Document 3: Japanese Patent Laid-Open No. 58-112930
Patent Document 4: Japanese Patent Laid-Open No. 3-224469
Patent Document 5: Japanese Patent Laid-Open No. 2001-39414

SUMMARY OF INVENTION

Problems to be Solved by the Invention

However, according to the conventional preform sterilization method, in some cases, the sterilizer is not uniformly deposited on the surface of the preform. If the sterilizer is not deposited in the form of a uniform coating on the surface of the preform, the surface of the preform and thus a container molded from the preform, such as a bottle, can be inadequately sterilized. Besides, the molded bottle can have a defect such as whitening.

If the flowrate of the mist or the like of the sterilizer is increased, the sterilizer can be uniformly deposited on the surface of the preform, and the sterilization effect can be improved. In that case, however, the amount of the sterilizer used increases, and more energy and time are required to remove the sterilizer. Thus, there is a problem that, if the energy and time are insufficient, the sterilizer remains on the preform and thus a container molded from the preform, such as a bottle. As a result, there is also a problem that the sterilization process takes longer.

An object of the present invention is to solve the problems described above. Furthermore, according to the conventional sterilization method for a container made of resin, in some cases, the sterilizer is not uniformly deposited on the surface of the container. If the sterilizer is not deposited in the form of a uniform coating on the surface of the container, the surface of the container can be inadequately sterilized.

If the flowrate of the mist or the like of the sterilizer is increased, the sterilizer can be uniformly deposited on the surface of the container, and the sterilization effect can be improved. In that case, however, the amount of the sterilizer used increases, and more energy and time are required to remove the sterilizer. Thus, there is a problem that, if the energy and time are insufficient, the sterilizer remains on the container. As a result, there is also a problem that the sterilization process takes longer.

Another object of the present invention is to solve the problems described above.

Means for Solving the Problems

To solve the problems described above, the present invention adopts the configurations described below.

Specifically, an invention according to claim 1 adopts a method of sterilizing a preform, wherein a sterilization process is performed on a preform that is made primarily of polyethylene terephthalate (PET) after a corona discharge treatment is performed on an inner surface of the preform, the corona discharge treatment including a voltage application step of applying a voltage produced in a corona discharge to an electrode that is capable of passing through an opening part of the preform, an insertion step of inserting the electrode to which the voltage is applied into the preform through the opening part, and a bottom part treatment step of treating an inner surface of a bottom part of the preform by bringing the electrode close to the bottom part until the corona discharge from the electrode changes discharge mode, and the sterilization process including a hydrogen peroxide supplying step of blasting a mist or gas of hydrogen peroxide solution or a mixture thereof to the preform.

As recited in claim 2, in the method of sterilizing a preform according to claim 1, the corona discharge treatment may be performed with a grounded conductor being provided around at least a part of the outside of the preform.

As recited in claim 3, in the method of sterilizing a preform according to claim 2, the corona discharge treatment may be performed with an insulator being provided between the preform and the conductor.

As recited in claim 4, in the method of sterilizing a preform according to claim 3, the corona discharge treatment may be performed with the insulator protruding beyond the conductor in a direction toward the opening part of the preform.

As recited in claim 5, in the method of sterilizing a preform according to any one of claims 1 to 4, the corona discharge treatment may be performed by bringing the electrode close to the inner surface of the bottom part of the preform while rotating the electrode and the preform with respect to each other about a central axis in the direction toward the opening part of the preform.

As recited in claim 6, in the method of sterilizing a preform according to any one of claims 1 to 5, the corona discharge treatment may be performed so that a contact angle with water of the surface of the preform is equal to or less than 75 degrees.

As recited in claim 7, in the method of sterilizing a preform according to any one of claims 1 to 6, the mist or gas of hydrogen peroxide or mixture thereof may be blasted to the preform after the preform is preliminarily heated by blasting heated air into the preform and blasting heated air to a thick part of the preform from outside of the preform.

As recited in claim 8, in the method of sterilizing a preform according to any one of claims 1 to 7, the mist or gas of hydrogen peroxide or mixture thereof may be produced by injecting a hydrogen peroxide solution and aseptic air into an evaporator from a twin fluid nozzle.

Furthermore, an invention according to claim 9 adopts a method of sterilizing a container made of resin, wherein a sterilization process is performed on a container made of resin after a corona discharge treatment is performed on an inner surface of the container made of resin, the corona discharge treatment including a voltage application step of applying a voltage produced in a corona discharge to an electrode that is capable of passing through an opening part of the container made of resin, an insertion step of inserting the electrode to which the voltage is applied into the container made of resin through the opening part, and a bottom part treatment step of treating an inner surface of a bottom part of the container made of resin by bringing the electrode close to the bottom part until the corona discharge from the electrode changes discharge mode, and the sterilization process including a hydrogen peroxide supplying step of blasting a mist or gas of hydrogen peroxide solution or a mixture thereof to the container made of resin.

As recited in claim 10, in the method of sterilizing a container made of resin according to claim 9, the opening part of the container made of resin may be narrow, and the corona discharge treatment may be performed on the inner surface of the container made of resin by an electrode that is expanded after the electrode enters the container made of resin through the opening part.

As recited in claim 11, in the method of sterilizing a container made of resin according to claim 9 or 10, the corona discharge treatment may be performed with a grounded conductor being provided around at least a part of the outside of the container made of resin.

As recited in claim 12, in the method of sterilizing a container made of resin according to claim 11, the corona discharge treatment may be performed with an insulator being provided between the container made of resin and the conductor.

As recited in claim 13, in the method of sterilizing a container made of resin according to claim 12, the corona discharge treatment may be performed with the insulator protruding beyond the conductor in a direction toward the opening part of the container made of resin.

As recited in claim 14, in the method of sterilizing a container made of resin according to any one of claims 9 to 13, the corona discharge treatment may be performed by bringing the electrode close to the inner surface of the bottom part of the container made of resin while rotating the electrode and the container made of resin with respect to each other about a central axis in the direction toward the opening part of the container made of resin.

As recited in claim 15, in the method of sterilizing a container made of resin according to any one of claims 9 to 14, at least the inner surface of the container made of resin may be made of polyolefin or polyethylene terephthalate.

As recited in claim 16, in the method of sterilizing a container made of resin according to any one of claims 9 to 15, the corona discharge treatment may be performed so that a contact angle with water of the surface of the container made of resin is equal to or less than 75 degrees.

As recited in claim 17, in the method of sterilizing a container made of resin according to any one of claims 9 to 16, the mist or gas of hydrogen peroxide or mixture thereof may be blasted to the container made of resin after the container made of resin is preliminarily heated by blasting heated air into the container made of resin and blasting heated air to a thick part of the container made of resin from outside of the container made of resin.

As recited in claim 18, in the method of sterilizing a container made of resin according to any one of claims 9 to 17, the mist or gas of hydrogen peroxide or mixture thereof may be produced by injecting a hydrogen peroxide solution and aseptic air into an evaporator from a twin fluid nozzle.

As recited in claim 19, in the method of sterilizing a container made of resin according to any one of claims 9 to 18, the sterilization process may include an air rinsing step performed after the hydrogen peroxide supplying step.

As recited in claim 20, in the method of sterilizing a container made of resin according to any one of claims 9 to 18, the sterilization process may include a water rinsing step performed after the hydrogen peroxide supplying step.

Advantageous Effects of Invention

Since the invention according to claim 1 is a method of sterilizing a preform, wherein a sterilization process is performed on a preform that is made primarily of polyethylene terephthalate (PET) after a corona discharge treatment is performed on an inner surface of the preform, the corona discharge treatment including a voltage application step of applying a voltage produced in a corona discharge to an electrode that is capable of passing through an opening part of the preform, an insertion step of inserting the electrode to which the voltage is applied into the preform through the opening part, and a bottom part treatment step of treating an inner surface of a bottom part of the preform by bringing the electrode close to the bottom part until the corona discharge from the electrode changes discharge mode, and the sterilization process including a hydrogen peroxide supplying step of blasting a mist or gas of hydrogen peroxide solution or a mixture thereof to the preform, the whole of the interior of the preform including the inner surface of the bottom part of the preform can be efficiently modified by bringing the electrode having passed through the opening part of the preform close to the inner surface of the bottom part of the preform to change the discharge mode of the corona discharge. In addition, a special gas such as argon does not need to be supplied, so that the cost can be reduced. In addition, since the electrode is brought closer to the inner surface of the bottom part of the preform until a discharge occurs along the inner surface of the bottom part of the preform, the entire inner surface of the bottom part of the preform is more readily modified. In addition, the bottom part is modified in a shorter time.

In the method of sterilizing a preform according to claim 1, if the corona discharge treatment is performed with a grounded conductor being provided around at least a part of the outside of the preform as recited in claim 2, the directivity of the discharge from the electrode to the preform is improved, and the inner surface of the preform can be more efficiently modified.

Note that, even if there is no grounded conductor, the corona treatment can be performed by changing the electrical characteristics or the shape of the electrode.

In the method of sterilizing a preform according to claim 2, if the corona discharge treatment is performed with an insulator being provided between the preform and the conductor as recited in claim 3, the discharge from the electrode is stabilized, and uniform modification is facilitated.

In the method of sterilizing a container according to claim 3, if the corona discharge treatment is performed with the insulator protruding beyond the conductor in a direction toward the opening part of the preform as recited in claim 4, a stable discharge from the electrode is ensured over the entire inner surface of the preform including the top of the opening part of the preform.

In the method of sterilizing a preform according to any one of claims 1 to 4, if the corona discharge treatment is performed by bringing the electrode close to the inner surface of the bottom part of the preform while rotating the electrode and the preform with respect to each other about a central axis in the direction toward the opening part of the preform as recited in claim 5, the surface treatment can be more uniformly achieved.

In the method of sterilizing a preform according to any one of claims 1 to 5, if the corona discharge treatment is performed so that a contact angle with water of the surface of the preform is equal to or less than 75 degrees as recited in claim 6, the wettability of the inner surface of the preform can be improved, and thus, the effect of sterilization of the inner surface can be further improved.

In the method of sterilizing a preform according to any one of claims 1 to 6, if the mist or gas of hydrogen peroxide or mixture thereof is blasted to the preform after the preform is preliminarily heated by blasting heated air into the preform and blasting heated air to a thick part of the preform from outside of the preform as recited in claim 7, the preform can be effectively sterilized since the mist or gas of hydrogen peroxide or a mixture thereof is blasted to the preform after the whole of the preform is uniformly heated.

In the method of sterilizing a preform according to any one of claims 1 to 7, if the mist or gas of hydrogen peroxide or mixture thereof is produced by injecting a hydrogen peroxide solution and aseptic air into an evaporator from a twin fluid nozzle as recited in claim 8, a fine mist of hydrogen peroxide is produced and deposited on the surface of the preform modified by the corona discharge treatment, so that a thin uniform coating of hydrogen peroxide solution is formed on the surface of the preform. Thus, the sterilization effect is improved.

Since the invention according to claim 9 is a method of sterilizing a container made of resin, wherein a sterilization process is performed on a container made of resin after a corona discharge treatment is performed on an inner surface of the container made of resin, the corona discharge treatment including a voltage application step of applying a voltage produced in a corona discharge to an electrode that is capable of passing through an opening part of the container made of resin, an insertion step of inserting the electrode to which the voltage is applied into the container made of resin through the opening part, and a bottom part treatment step of treating an inner surface of a bottom part of the container made of resin by bringing the electrode close to the bottom part until the corona discharge from the electrode changes discharge mode, and the sterilization process including a hydrogen peroxide supplying step of blasting a mist or gas of hydrogen peroxide solution or a mixture thereof to the container made of resin, the whole of the interior of the container made of resin including the inner surface of the bottom part of the container made of resin can be efficiently modified by bringing the electrode having passed through the opening part of the container made of resin close to the inner surface of the bottom part of the container made of resin to change the discharge mode of the corona discharge. In addition, a special gas such as argon does not need to be supplied, so that the cost can be reduced.

In addition, since the electrode is brought closer to the inner surface of the bottom part of the container made of resin until a discharge occurs along the inner surface of the bottom part of the container made of resin, the entire inner surface of the bottom part of the container made of resin is more readily modified. In addition, the bottom part is modified in a shorter time.

In the method of sterilizing a container made of resin according to claim 9, if the opening part of the container made of resin is narrow, and the corona discharge treatment is performed on the inner surface of the container made of resin by an electrode that is expanded after the electrode enters the container made of resin through the opening part as recited in claim 10, the tip end of the electrode is opened and comes close to the inner surface of the side wall part of the container made of resin after passing through the opening part of the container made of resin, so that the inner surface of the side wall part of the container made of resin can be efficiently modified.

In the method of sterilizing a container made of resin according to claim 9 or 10, if the corona discharge treatment is performed with a grounded conductor being provided around at least a part of the outside of the container made of resin as recited in claim 11, the directivity of the discharge from the electrode to the container made of resin is improved, and the inner surface of the container made of resin can be more efficiently modified.

Note that, even if there is no grounded conductor, the corona treatment can be performed by changing the electrical characteristics or the shape of the electrode.

In the method of sterilizing a container made of resin according to claim 11, if the corona discharge treatment is performed with an insulator being provided between the container made of resin and the conductor as recited in claim 12, the discharge from the electrode is stabilized, and uniform modification is facilitated.

In the method of sterilizing a container according to claim 12, if the corona discharge treatment is performed with the insulator protruding beyond the conductor in a direction toward the opening part of the container made of resin as recited in claim 13, a stable discharge from the electrode is ensured over the entire inner surface of the container made of resin including the top of the opening part of the container made of resin.

In the method of sterilizing a container made of resin according to any one of claims 9 to 13, if the corona discharge treatment is performed by bringing the electrode close to the inner surface of the bottom part of the container made of resin while rotating the electrode and the container made of resin with respect to each other about a central axis in the direction toward the opening part of the container made of resin as recited in claim 14, the surface treatment can be more uniformly achieved.

In the method of sterilizing a container made of resin according to any one of claims 9 to 14, if at least the inner surface of the container made of resin is made of polyolefin or polyethylene terephthalate as recited in claim 15, the wettability of the inner surface of the container made of resin is extremely low. Even in such a case, however, the effect of sterilization of the inner surface can be further improved.

In the method of sterilizing a container made of resin according to any one of claims 9 to 15, if the corona discharge treatment is performed so that a contact angle with water of the surface of the container made of resin is equal to or less than 75 degrees as recited in claim 16, the wettability of the inner surface of the container made of resin can be improved, and thus, the effect of sterilization of the inner surface can be further improved.

In the method of sterilizing a container made of resin according to any one of claims 9 to 16, if the mist or gas of hydrogen peroxide or mixture thereof is blasted to the container made of resin after the container made of resin is preliminarily heated by blasting heated air into the container made of resin and blasting heated air to a thick part of the container made of resin from outside of the container made of resin as recited in claim 17, the container made of resin can be effectively sterilized since the mist or gas of hydrogen peroxide or a mixture thereof is blasted to the container made of resin after the whole of the container made of resin is uniformly heated.

In the method of sterilizing a container made of resin according to any one of claims 9 to 17, if the mist or gas of hydrogen peroxide or mixture thereof is produced by injecting a hydrogen peroxide solution and aseptic air into an evaporator from a twin fluid nozzle as recited in claim 18, a fine mist of hydrogen peroxide is produced and deposited on the surface of the container made of resin modified by the corona discharge treatment, so that a thin uniform coating of hydrogen peroxide solution is formed on the surface of the container made of resin. Thus, the sterilization effect is improved.

In the method of sterilizing a container made of resin according to any one of claims 9 to 18, if the sterilization process includes an air rinsing step performed after the hydrogen peroxide supplying step as recited in claim 19, the amount of hydrogen peroxide remaining on the container made of resin can be reduced, and foreign matters can be removed.

In the method of sterilizing a container made of resin according to any one of claims 9 to 18, if the sterilization process includes a water rinsing step performed after the hydrogen peroxide supplying step as recited in claim 20, the amount of hydrogen peroxide remaining on the container made of resin can be reduced, and foreign matters can be removed.

BRIEF DESCRIPTION OF THE DRAWINGS

FIG. 5A is a schematic diagram showing how a corona discharge treatment is performed in the apparatus shown in FIG. 1.

FIG. 5C is a schematic diagram showing how the corona discharge treatment is performed in the apparatus shown in FIG. 1.

FIG. 7 are diagrams for illustrating a treatment on the preform, in which FIG. 7(A) shows a preform preliminary heating step, FIG. 7(B) shows a preform hydrogen peroxide supplying step, and FIG. 7(C) shows a preform heating step.

FIG. 8 are diagrams for illustrating a process following the preform heating step, in which FIG. 8(D) shows a container molding step, FIG. 8(E) shows a container preliminary heating step, FIG. 8(F) shows a container hydrogen peroxide supplying step, and FIG. 8(G1) shows an air rinsing step.

FIG. 9 are diagrams for illustrating a process following the container hydrogen peroxide supplying step, in which FIG. 9(G2) shows a modification of the air rinsing step, FIG. 9(H) shows a water rinsing step, FIG. 9(I) shows a content filling step, and FIG. 9(J) shows a sealing step.

FIGS. 15(A) to 15(E) are schematic diagrams showing modifications of an electrode shown in FIG. 11.

FIGS. 16(A) to 16(E) are schematic diagram showing a modification of a step of inserting the electrode.

FIG. 20 are diagrams showing a sterilization process performed on the container made of resin, in which FIG. 20(A) shows a preliminary heating step, FIG. 20(B) shows a hydrogen peroxide supplying step, FIG. (C1) shows an air rinsing step, and FIG. 20(C2) shows a modification of the air rinsing step.

FIG. 21 are diagrams for illustrating the sterilization process performed on the container made of resin, filling of the container made of resin with a content, and sealing of the container made of resin, in which FIG. 21(D) shows a water rinsing step, FIG. 21(E) shows a content filling step, and FIG. 21(F) shows a sealing step.

BEST MODE FOR CARRYING OUT THE INVENTION

In the following, embodiments of the present invention will be described with reference to the drawings.

First Embodiment

First, a configuration and general functions of an apparatus that performs a corona discharge treatment on a preform yet to be molded into a bottle will be described with reference to FIGS. 1 to 3.

The preform is a preliminarily formed body yet to be molded into a bottle as a container.

Figure 1:
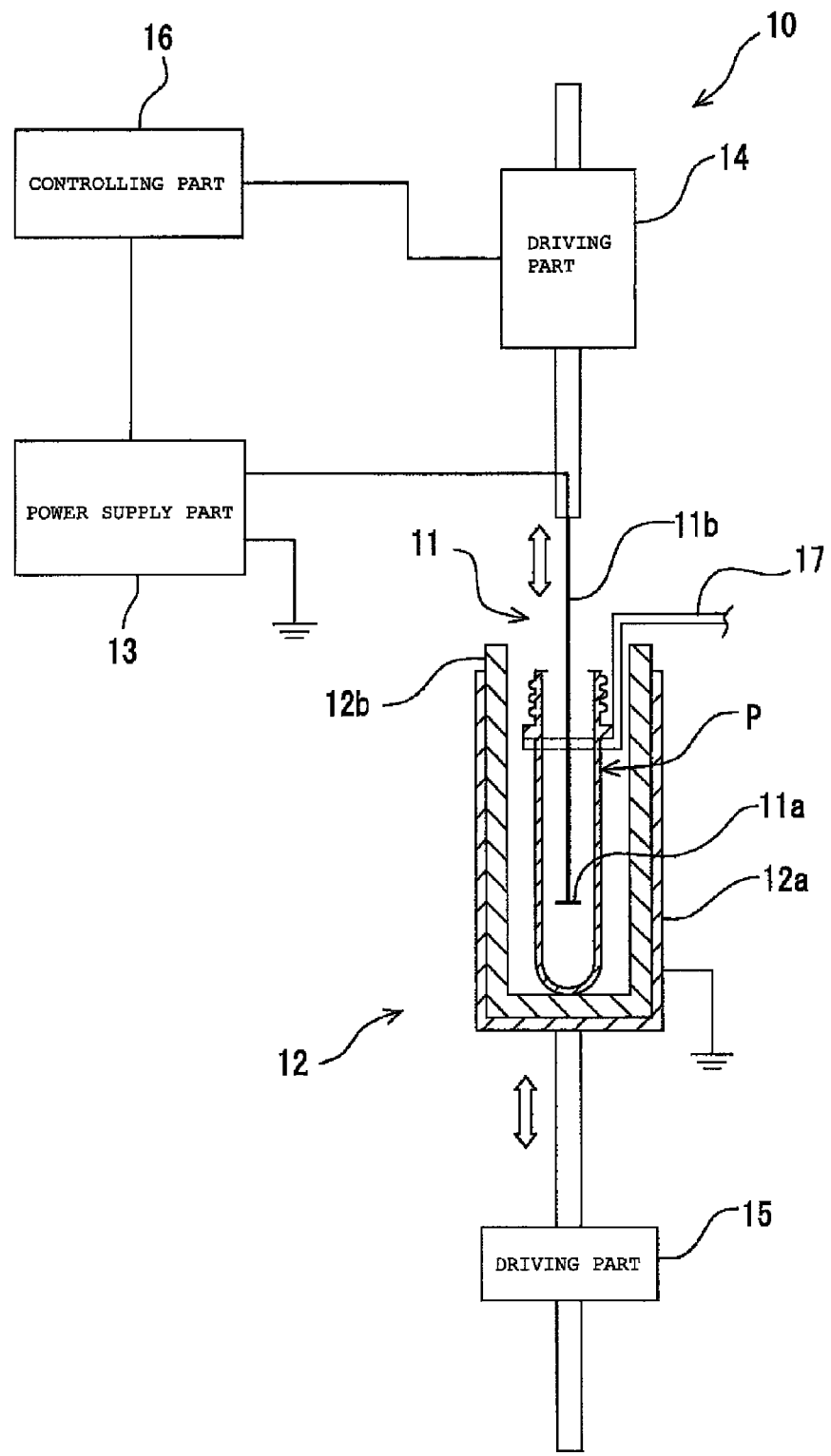
FIG. 1 is a schematic diagram showing an example of an apparatus for performing a corona discharge treatment on a preform.

As shown in FIG. 1, a corona discharge treatment apparatus 10 includes an electrode 11 that can pass through an opening part of a preform, a grounding part 12 that is grounded, a power supply part 13 that applies to the electrode 11 a voltage produced in a corona discharge, a driving part 14 that inserts the electrode 11 into a preform P, a driving part 15 that drives the grounding part 12 to cover the preform P, and a controlling part 16 that controls operation of the driving parts 14 and 15.

The corona discharge treatment apparatus 10 modifies an inner surface of the preform P with a corona discharge. For example, electrons emitted from the electrode 11 in a corona discharge are accelerated in the electrical field and collide with electrons or molecules in the air to cause excitation, dissociation or ionization of atoms or molecules. The ionized atoms or molecules also emit electrons. Upon reaching a surface layer of a resin, electrons cleave main or side chains of the polymer. The surface layer of the polymer in which main or side chains are cleaved is chemically radical. When oxygen radicals, ozone molecules or the like in the gas phase are combined with the main or side chains, polar functional groups, such as hydroxyl groups or carbonyl groups, are introduced to impart hydrophilicity to the surface layer of the resin, thereby improving the wettability. In this way, the surface of the resin is modified.

The preform P is held at a predetermined position in the corona discharge treatment apparatus 10 by a holding part 17.

Figure 2:
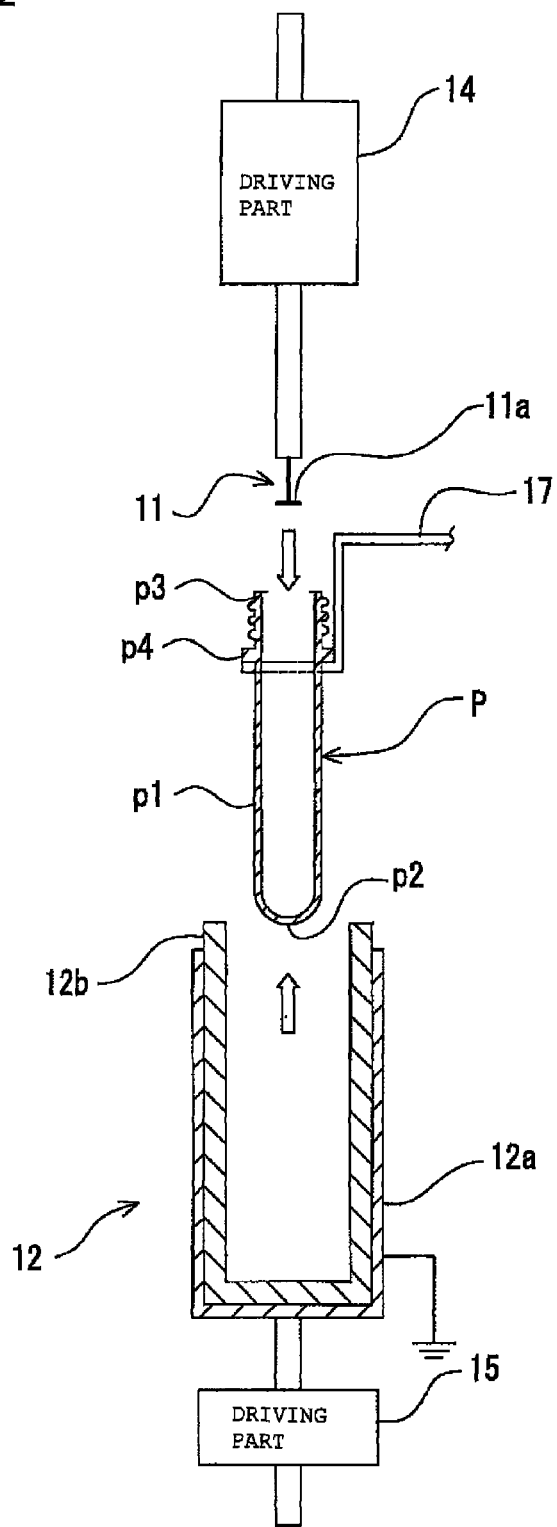
FIG. 2 is a schematic diagram showing an example of the apparatus shown in FIG. 1 in which the preform is set.

As shown in FIG. 2, the preform P has the shape of a test tube, and has a trunk part p1, a bottom part p2 that closes the bottom of the trunk part p1, and at least one opening part p3 provided opposite to the bottom part p2.

The trunk part p1 of the preform P has a substantially cylindrical shape, for example. The trunk part p1 of the preform P may have another shape, such as a square cylindrical shape.

The opening part p3 has a tubular shape and has a male thread formed on the outer side. As shown in FIG. 9(J), a female thread of a cap C can be engaged with the female thread of the opening part p3. A bottle B molded from the preform P is closed by the engagement of the male and female threads. In addition, a flange-shaped support ring p4 is formed on the outer side of the opening part p3. The preform P or bottle B is suspended by the holding part 17 with the support ring p4 hooked on the holding part 17.

The preform P is made primarily of polyethylene terephthalate and is formed by a single layer of this resin. Alternatively, the preform P may be made of a mixture of polyethylene terephthalate and polyamide or polyglycolic acid or may be formed by a multilayer structure of these materials. The bottle B molded from the preform P may have a volume of 500 mL, for example.

Figure 3:
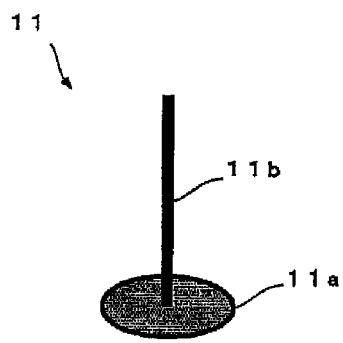
FIG. 3 is a schematic diagram showing an example of an electrode of the apparatus shown in FIG. 1.

As shown in FIG. 3, the electrode 11 has an electrode discharge part 11a and an electrode post 11b.

The electrode 11 is a conductor made of metal, such as stainless steel. The electrode 11 has a shape and size that allows the electrode 11 to pass through the opening part of the preform P and has a length that allows the electrode 11 to come close to the inner surface of the bottom part of the preform P. For example, the electrode discharge part 11a has a disk-like shape and has a diameter smaller than the inner diameter of the opening part p3 of the preform P, and the electrode post 11b has a length that allows the electrode discharge part 11a to come close to the inner surface of the bottom part p2 of the preform P.

The grounding part 12 (which is an example of a conductor grounded) has a conductive part 12a, which is a conductor made of metal such as stainless steel, and an insulating part 12b, which is made of resin or the like. Examples of the conductor include stainless steel, iron, copper, brass, aluminum, a gold-plated metal, carbon, or a conductive polymer.

The conductive part 12a (which is an example of a grounded conductor provided around at least a part of the outside of the bottle) has a bottom part and is shaped to cover the bottom part p2 and the trunk part p1 of the preform P. For example, if the trunk part p1 of the preform P has a cylindrical shape, the conductive part 12a also has a cylindrical shape but is larger than the preform P. The conductive part 12a is grounded.

The insulating part 12b (which is an example of an insulator between the bottle and the conductor) is made of resin and has a predetermined thickness. The insulating part 12b is located between the preform P and the conductive part 12a and serves as a spacer. For example, the insulating part 12b has a bottom part and is shaped on the inner side to receive the preform P and on the outer side to be housed in the conductive part 12a. The insulating part 12b is in contact with the conductive part 12a at a part of the circumferential surface thereof and at the bottom part thereof.

Examples of the material of the insulating part 12b include a phenol resin, an epoxy resin, polypropylene, polyethylene, or polyethylene terephthalate.

The insulating part 12b protrudes beyond the conductive part 12a in the direction of the opening of the preform P. In other words, the length (depth) of the insulating part 12b in the lengthwise direction is greater than the height of the preform P.

The length (depth) of the conductive part 12a in the lengthwise direction is preferably approximately equal to the height of the opening part p3 of the preform P in the state where the insulating part 12b exists.

The power supply part 13 is a power supply that generates a high voltage at a constant voltage, a constant current or a constant power. The power supply part 13 has a converter that performs frequency conversion to raise the frequency of the commercial power supply, a high-voltage transformer that boosts the voltage to the voltage of the corona discharge, and the like. The power supply part 13 applies a high voltage produced in the corona discharge to the electrode 11.

The driving part 14 (which is an example of a driving device) has a motor, such as a servo motor. The driving part 14 is coupled to the electrode 11. As shown in FIG. 2, the driving part 14 performs a driving operation to insert the electrode 11 into the preform P through the opening part of the preform P. The driving part 14 then performs a driving operation to bring the electrode 11 close to the inner surface of the bottom part of the preform P and then withdraw the electrode 11 from the preform P. The driving part 14 may rotate the electrode 11 about an axis of the electrode 11 in the lengthwise direction (the direction of the opening of the preform P) while inserting or withdrawing the electrode 11 into or from the preform P.

The driving part 15 (which is an example of a driving device) has a motor, such as a servo motor. The driving part 15 is coupled to the bottom part of the grounding part 12. As shown in FIG. 2, the driving part 15 drives the grounding part 12 to cover the preform P from the bottom thereof. After a discharge treatment, the driving part 15 drives the grounding part 12 to remove the grounding part 12 from around the preform P. The driving part 15 may rotate the grounding part 12 with the preform P set therein about the axis of the electrode 11 in the lengthwise direction (the direction of the opening of the preform P) along with the preform P.

The controlling part 16 has a central processing unit (CPU) and a memory. The CPU controls turn on/off, voltage or the like of the power supply part 13 according to a program stored in the memory and controls driving operations of the driving parts 14 and 15. The controlling part 16 can also control operation of the holding part 17.

Next, a surface treatment on the preform P by the corona discharge treatment apparatus 10 will be described with reference to FIGS. 4 to 5E.

Figure 4:
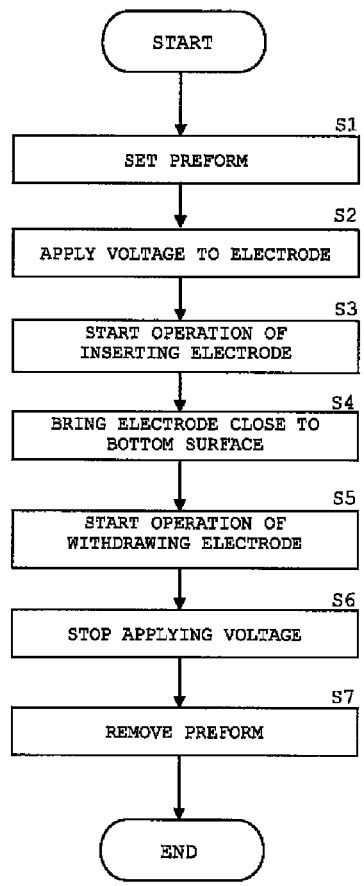
FIG. 4 is a flowchart showing an example of an operation of the apparatus shown in FIG. 1.

As shown in FIG. 4, the preform P is set in the corona discharge treatment apparatus 10 (Step S1). More specifically, a conveyor (not shown) for the preform P conveys the preform P to the corona discharge treatment apparatus 10.

As shown in FIG. 2, the preform P held by the holding part 17 is set at a predetermined position in the corona discharge treatment apparatus 10. The corona discharge treatment apparatus 10 checks whether the preform P is set at the predetermined position, using a sensor or the like (not shown).

Under the control of the controlling part 16 of the corona discharge treatment apparatus 10, the driving part 15 then drives the grounding part 12 in the direction of the opening of the preform P so that the preform P is housed in the grounding part 12 from the bottom part p2 of the preform P. As shown in FIG. 5A, the preform P is thus housed in the grounding part 12. At this point in time, the preform P is held by the holding part 17, although not shown.

The corona discharge treatment apparatus 10 then applies a voltage to the electrode 11 (Step S2).

More specifically, under the control of the controlling part 16 of the corona discharge treatment apparatus 10, the power supply part 13 applies a voltage to the electrode 11 so that the electrode discharge part 11a of the electrode 11 produces a corona discharge in the air. As shown in FIG. 5A, a corona discharge C1 occurs at a circumferential part of the disk of the electrode discharge part 11a. Since the electrode discharge part 11a is spaced apart from the conductive part 12a of the grounding part 12, the corona discharge C1 is in a discharge mode of low directivity.

The corona discharge treatment apparatus 10 then starts an operation of insertion of the electrode 11 (Step S3).

More specifically, under the control of the controlling part 16, the driving part 14 for the electrode 11 starts an operation of insertion of the electrode 11 producing a corona discharge. The driving part 14 may rotate the electrode 11 during the insertion. Alternatively, the driving part 15 may rotate the grounding part 12 along with the preform P so that the preform P and the electrode 11 rotate with respect to each other.

Figure 5B:
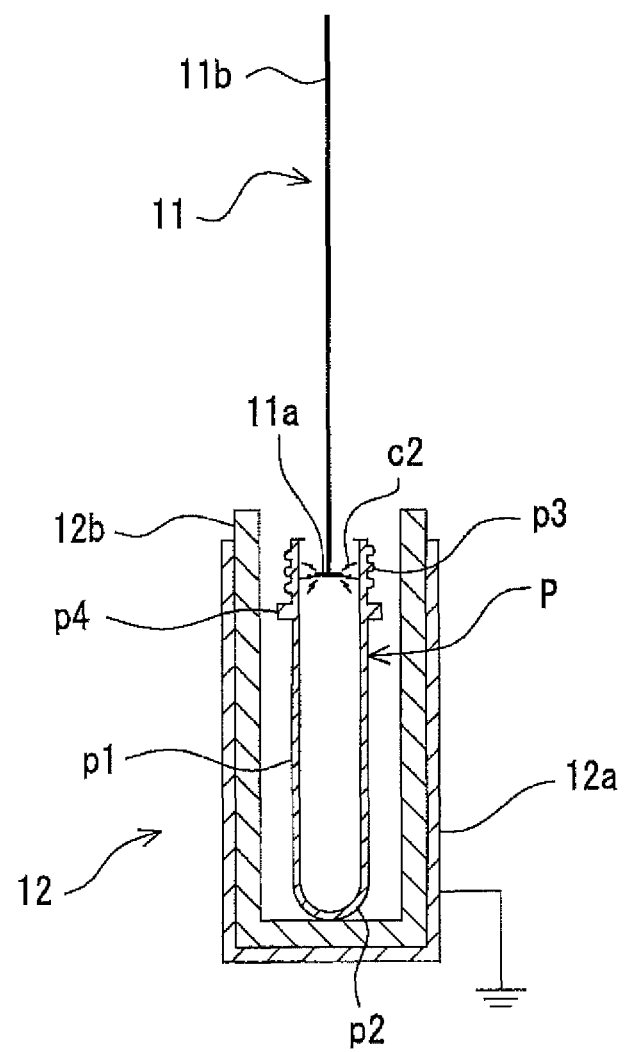
FIG. 5B is a schematic diagram showing how the corona discharge treatment is performed in the apparatus shown in FIG. 1.

As the electrode discharge part 11a comes closer to the conductive part 12a, the corona discharge changes to a discharge mode with higher directivity to the conductive part 12a. As shown in FIG. 5B, when the electrode discharge part 11a enters the opening part p3 of the preform P, the corona discharge occurring at the circumferential part of the electrode discharge part 11a changes to a corona discharge C2 in a discharge mode of higher directivity. The corona discharge C2 is in a discharge mode of high directivity. As the electrode discharge part 11a passes through the narrower interior of the opening part p3 of the preform P, the surface of the interior of the opening part p3 is modified by the corona discharge C2.

The surface of the interior of the opening part p3 of the preform P and the circumferential part of the electrode discharge part 11a are close to each other. Thus, the driving part 14 may quickly pass the electrode discharge part 11a through the interior of the opening part p3.

As shown in FIG. 5C, the driving part 14 further inserts the electrode 11 into the preform P. As the electrode 11 is inserted deeper into the preform P, the inner surface of the trunk part p1 of the preform P is modified by the corona discharge C2.

The corona discharge treatment apparatus 10 then bring the electrode 11 close to the bottom surface of the preform P to treat the inner surface of the bottom part p2 of the preform P (Step S4).

More specifically, under the control of the controlling part 16, the driving part 14 for the electrode 11 brings the electrode discharge part 11a close to the inner surface of the bottom part p2 of the preform P.

Figure 5D:
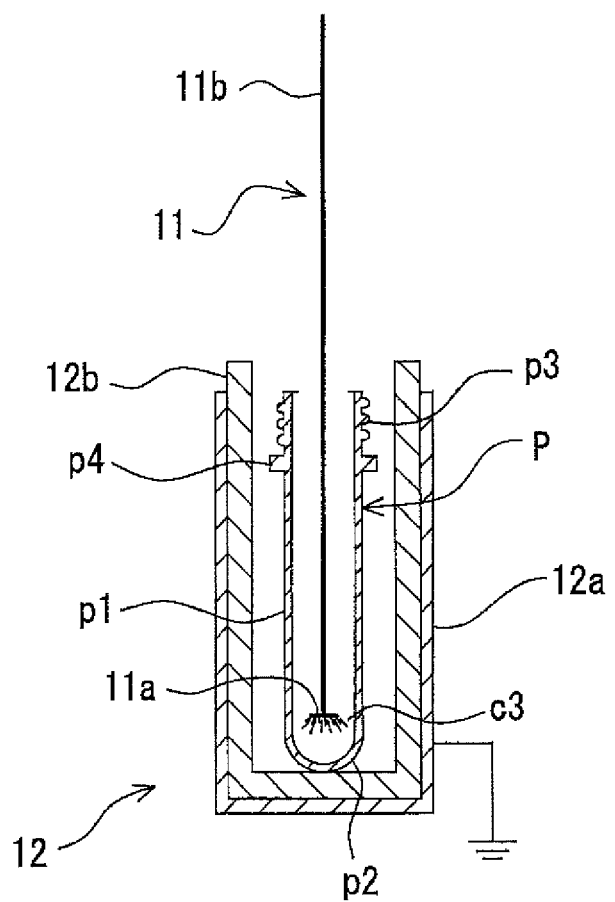
FIG. 5D is a schematic diagram showing how the corona discharge treatment is performed in the apparatus shown in FIG. 1.

As shown in FIG. 5D, when the electrode discharge part 11a comes close to the inner surface of the bottom part p2 of the preform P, a corona discharge C3, which is a surface discharge, occurs at a circular surface part (a surface opposed to the bottom surface of the conductive part 12a) of the electrode discharge part 11a. The corona discharge C3 (which is an example of a discharge for treatment of the inner surface of the bottom part p2 of the preform P), which is a surface discharge, occurs at the surface part of the electrode discharge part 11a because the impedance between the surface part of the electrode discharge part 11a and the conductive part 12a of the grounding part 12 is lower than the impedance between the circumferential part of the electrode discharge part 11a and the conductive part 12a of the grounding part 12. In other words, the corona discharge changes the discharge mode from the corona discharge C2 to the corona discharge C3.

The inner surface of the bottom part p2 of the preform P starts being modified by the corona discharge C3, which is a surface discharge.

The driving part 14 or 15 may rotate the electrode 11 and the preform P with respect to each other about the axis in the direction of the opening of the preform P while bringing the electrode 11 close to the inner surface of the bottom part p2 of the preform P.

Figure 5E:
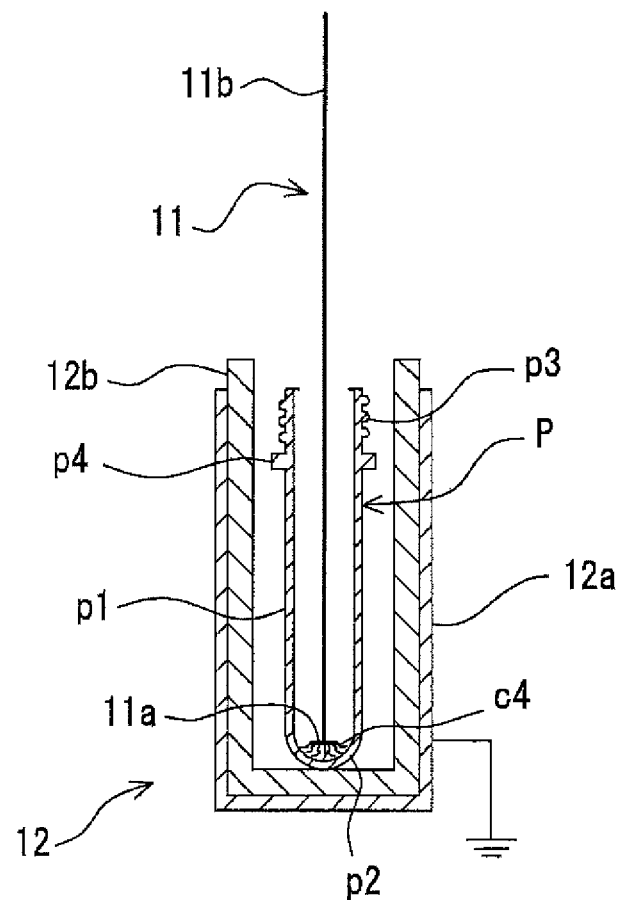
FIG. 5E is a schematic diagram showing how the corona discharge treatment is performed in the apparatus shown in FIG. 1.

As the electrode discharge part 11a comes closer to the inner surface of the bottom part p2 of the preform P, as shown in FIG. 5E, the corona discharge changes the discharge mode from the corona discharge C3 to a discharge C4 (which is an example of the discharge for treatment of the inner surface of the bottom part p2 of the preform P). The discharge C4 is a surface discharge that occurs along the inner surface of the bottom part p2. The discharge is the corona discharge that is produced from the surface part of the electrode discharge part 11a and spreads over the entire inner surface of the bottom part p2 along the inner surface of the bottom part p2 of the preform P. The discharge C4 facilitates modification of the entire inner surface of the bottom part p2.

The corona discharge treatment apparatus 10 then starts an operation of withdrawing the electrode 11 (Step S5). More specifically, under the control of the controlling part 16, the driving part 14 for the electrode 11 starts the operation of withdrawing the electrode 11 producing the corona discharge. As the electrode 11 is withdrawn, the discharge mode changes from the discharge C4 to the corona discharge C3 and then from the corona discharge C3 to the corona discharge C2. The inner surface of the preform P is also modified during the operation of withdrawing the electrode 11. The driving part 14 may rotate the electrode 11 while withdrawing the electrode 11. Alternatively, application of the voltage can be stopped when the operation of withdrawing the electrode 11 is performed.

The corona discharge treatment apparatus 10 then stops application of the voltage (Step S6).

More specifically, under the control of the controlling part 16, the power supply part 13 stops applying the voltage to the electrode 11 to stop production of the corona discharge when the electrode 11 is positioned again as shown in FIG. 5A.

The interior of the opening part p3 of the preform P is closer to the circumferential part of the electrode discharge part 11a and is more readily modified. Thus, the power supply part 13 can stop applying the voltage to the electrode 11 when the electrode 11 is positioned as shown in FIG. 5B.

The corona discharge treatment apparatus 10 removes the preform P (Step S7).

Under the control of the controlling part 16, the driving part 14 drives the grounding part 12 so that the preform P is removed from the grounding part 12. The preform P held by the holding part 17 is removed from the predetermined position in the corona discharge treatment apparatus 10, and the preform P is then conveyed by a conveyor to a position for the subsequent step.

As described above, according to this embodiment, the electrode 11 having passed through the opening part p3 of the preform P is brought close to the inner surface of the bottom part p2 of the preform P, and the mode of the corona discharge is changed so that the bottom part p2 of the preform P can also be efficiently treated. Thus, the whole of the interior of the preform P can be efficiently modified. In addition, the corona discharge can be produced in the normal air, and a special gas such as argon does not need to be supplied, so that the cost can be reduced.

If the electrode 11 is brought closer to the inner surface of the bottom part p2 of the preform P until the discharge C4 occurs along the inner surface of the bottom part p2 of the preform P, the entire inner surface of the bottom part p2 is more readily modified. In addition, the bottom part p2 is modified in a shorter time.

If there is the grounded conductive part 12a (which is an example of the conductor) around at least part of the outside of the preform P, the directivity of the discharge from the electrode discharge part 11a to the preform P is improved, and the inner surface of the preform P can be more efficiently modified.

If there is the insulating part 12b (which is an example of the insulator) between the preform P and the conductive part 12a, the discharge from the electrode discharge part 11a is stabilized, and uniform modification is facilitated.

If the insulating part 12b (which is an example of the insulator) protrudes beyond the conductive part 12a (which is an example of the conductor) in the direction of the opening of the preform P, a stable discharge from the electrode 11 is ensured over the entire inner surface of the preform P including the top of the opening part p3 of the preform P, so that appropriate surface treatment can be achieved.

If the electrode 11 and the preform P are rotated with respect to each other about the axis in the direction of the opening of the preform P when the electrode 11 is brought close to the inner surface of the bottom part p2 of the preform P, the surface treatment can be more uniformly achieved.

By the corona discharge treatment described above, the inner surface of the preform P is modified to have higher wettability. More specifically, the inner surface modified by the corona discharge treatment has a contact angle with water of approximately 75 degrees or less, whereas the inner surface yet to be modified has a contact angle with water of approximately 80 degrees, for example.

The preform P whose inner surface has been modified by the corona discharge treatment as described above is subjected to a sterilization process described below immediately or after being housed and stored in a container or the like along with many other preforms P modified and molded in the same manner.

More specifically, as shown in FIG. 7(A), the preform P is subjected to a preform preliminary heating step, in which the preform P is supplied with heated air H through a nozzle 21 and preliminarily heated to a preliminary sterilization temperature.

As shown in FIG. 7(B), the preform P is then subjected to a preform hydrogen peroxide supply step, in which a mist M or gas G of hydrogen peroxide solution or a mixture thereof is blasted from a nozzle 22 to the preform P to sterilize the preform P.

Figure 10:
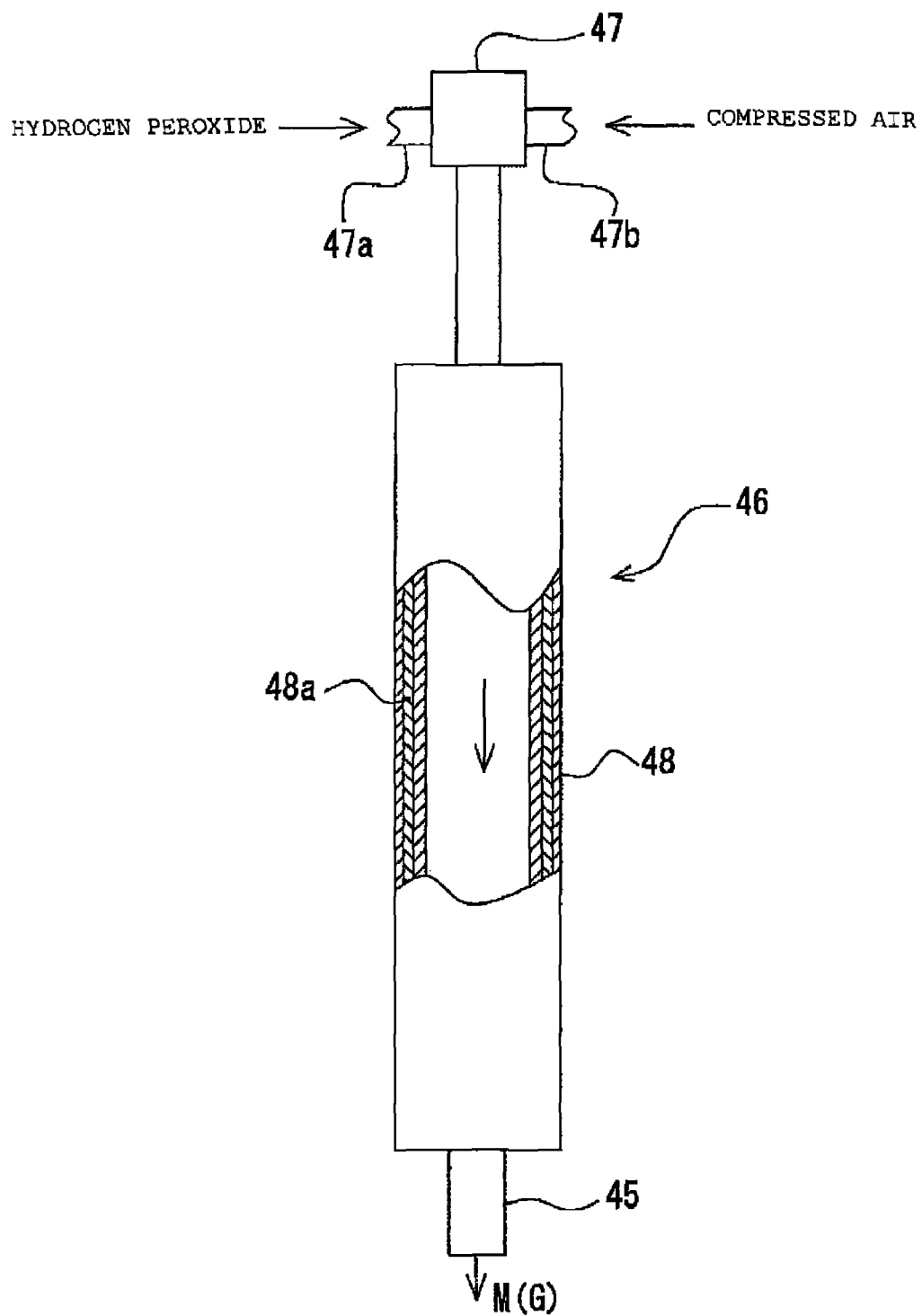
FIG. 10 is a partially cut-away diagram showing a producer that produces a mist or gas of hydrogen peroxide solution or a mixture thereof.

The mist M or gas G of hydrogen peroxide solution or mixture thereof is produced by a producer 46 shown in FIG. 10, for example. The hydrogen peroxide solution is an aqueous solution containing 20% by weight to 60% by weight of hydrogen peroxide and also contains an additive, such as a stabilizer. The concentration of hydrogen peroxide is preferably 35% by weight.

The producer 46 includes a hydrogen peroxide solution supplying part 47 that serves as a twin fluid sprayer that atomizes the aqueous solution of hydrogen peroxide serving as a sterilizer and supplies the resulting spray, and an evaporating part 48 that evaporates the spray of hydrogen peroxide solution supplied from the hydrogen peroxide solution supplying part 47 by heating the spray to a temperature equal to or higher than the boiling point of the hydrogen peroxide solution and equal to or lower than the non-degradable temperature thereof. The hydrogen peroxide solution supplying part 47 is configured to receive hydrogen peroxide solution and compressed air through a hydrogen peroxide solution supply channel 47a and a compressed air supply channel 47b, respectively, and spray the hydrogen peroxide solution into the evaporating part 48. The evaporating part 48 is a pipe with a heater 48a interposed between an inner wall and an outer wall thereof, and heats and evaporates the spray of hydrogen peroxide solution blasted into the pipe. The gas G of hydrogen peroxide solution resulting from the evaporation is ejected to the opening of the opening part p3 of the preform P from the nozzle 45 in the form of the mist M or gas G or mixture thereof.

As shown in FIG. 7(B), some of the mist M or gas G or mixture thereof ejected from the nozzle 22 enters the preform P through the opening part p3, and some flows down on the exterior of the preform P.

Thus, most of the microorganisms on the surface of the preform P are killed except for some on the inner surface of the opening part p3.

As shown in FIG. 7(C), the sterilized preform P is subjected to a preform heating step, in which the preform P is heated to a molding temperature by a heater 23. The hydrogen peroxide on the preform P having been activated by the preliminary heating described above is further activated by this heating, and the sterilization effect of the hydrogen peroxide is improved. Air at room temperature or heated air may be blasted to the part of the preform P on which there is hydrogen peroxide to remove the hydrogen peroxide solution or improve the sterilization effect of the hydrogen peroxide.

As shown in FIG. 8(D), the preform P heated to a predetermined temperature is blow-molded into the bottle B (see FIG. 8(E)) in a die 24. In FIG. 8(D), reference numeral 9 denotes an extension rod. Although the opening part p3 and the support ring p4 of the preform p retain their shape when the preform P is molded into the bottle 2, the trunk part p1 and the bottom part p2 of the preform P are expanded into a trunk part b1 and a bottom part b2 of the bottle B having a smaller thickness as a result of the blow molding.

After the blow molding, the bottle 2 is removed from the die 24 and is subjected to a sterilization process immediately or after being housed and stored in a container or the like along with many other bottles 2 molded in the same manner. Alternatively, the bottle 2 may not be fed to the sterilization process but may be filled in an aseptic condition with a sterilized content by a filler connected to the molding machine and sealed with a sterilized cap.

The opening part and the support ring of the bottle B are the same in shape or the like as the opening part p3 and the support ring p4 of the preform P and therefore denoted by the same reference characters.

As shown in FIG. 8(E), the blow-molded bottle B is subjected to a container preliminary heating step, in which a nozzle 43 is inserted into the bottle B through the opening part p3 of the bottle B. Heated air is fed into the bottle B from the nozzle 43.

If the bottle B is fed to the subsequent sterilization process immediately after blow molding, the bottle B is still warm as a result of the heating of the preform P, so that the container preliminary heating step can be omitted.

In the preliminary heating, nozzles 44, 44 are installed to be opposed to the outer surface of the opening part p3 of the bottle B, and heated air is blasted from the nozzles 44, 44 to the opening part p3 to further heat the opening part p3. This is because the opening part p3 and the support ring p4 are relatively thick and cannot be sufficiently heated only by the heated air from the nozzle 43.

The nozzle 43 is inserted into the bottle B in order to ensure that the heated air be fed into the bottle B. The extent to which the nozzle 43 is inserted can be appropriately changed depending on the flowrate of the heated air, the diameter of the opening part p3 or the like. However, as shown in FIG. 8(A), the tip end of the nozzle 43 is preferably located in the bottle diameter transition region between the opening part p3 and the trunk part b1 of the bottle B. The transition region can be defined as a region from the lower end of the opening part p3 to a level at which the diameter of the bottle is 70% of the maximum diameter of the bottle, for example. The preliminary heating is desirably performed until the temperature of the inner surface of the bottle B becomes 40° C. or higher.

The container preliminary heating described above is performed as required, and can be omitted.

The preliminarily heated bottle B is conveyed for a container hydrogen peroxide supply step.

In the hydrogen peroxide supply step, as shown in FIG. 8(F), the mist M or gas G of hydrogen peroxide solution or mixture thereof is supplied into the bottle B from the nozzle 45.

The mist M or gas G of hydrogen peroxide solution or mixture thereof is produced by a machine similar to the producer 46 described above.

As shown in FIG. 8(F), the mist M or gas G or mixture thereof ejected from the nozzle 45 enters the bottle B through the opening part p3 and flows down on the outer surface of the bottle B.

Thus, the fine mist M of hydrogen peroxide solution is deposited on the inner and outer surfaces of the bottle B. As described above, the inner surface of the bottle B is modified by the corona discharge treatment before the bottle B is molded from the preform P. Thus, when the mist M is deposited on the inner surface of the bottle B, in particular, the hydrogen peroxide solution is spread to form a uniform thin coating on the entire inner surface of the bottle B. Thus, nonuniform sterilization is prevented, and the sterilization effect is improved.

If the bottle B is heated in the preliminary heating described above, not only the inner surface but also the outer surface of the bottle B is effectively sterilized by the hydrogen peroxide.

The amount of deposition of the mist of hydrogen peroxide solution per bottle with a volume of 500 mL preferably ranges from 5 μL to 100 μL of a 35%-by-weight hydrogen peroxide solution. That is, the amount of the mist M is preferably set so that the same amount of hydrogen peroxide as the hydrogen peroxide contained in 5 μL to 100 μL of a hydrogen peroxide solution containing 35% by weight of hydrogen peroxide is deposited on the interior of the bottle B. The duration of the blasting of the mist M preferably ranges from 0.1 seconds to 1 second per bottle.

As shown in FIG. 8(B), a tunnel 49 through which the bottle B passes is provided below the nozzle 45, as required. Since the tunnel 49 is filled with the mist M of hydrogen peroxide solution, the mist M of hydrogen peroxide solution is more readily deposited on the outer surface of the bottle B, and the effect of sterilization of the outer surface of the bottle B is improved accordingly.

As shown in FIG. 8(G1), the bottle B is subjected to an air rinsing step.

The air rinsing step is performed by blasting aseptic air N into the bottle B from a nozzle 50. The hydrogen peroxide, foreign matter and the like are removed from the bottle B by the flow of the aseptic air N.

Although the aseptic air N is desirably hot air obtained by heating air, the aseptic air N may be at room temperature. If the hot air is blasted into the bottle B, the interior of the bottle B is heated, and the sterilization effect of the mist M of hydrogen peroxide solution is improved, and penetration of the hydrogen peroxide into the surface of the bottle B is suppressed and the hydrogen peroxide is likely to remain on the inner surface of the bottle B. In addition, the mist floating in the bottle B is discharged by the hot air to the outside of the bottle B. At this point in time, sterilization has been sufficiently achieved by the mist M of hydrogen peroxide solution deposited on the inner surface of the bottle B, and thus, the sterilization effect is not compromised by discharging the mist M floating in the inner space of the bottle B. Rather, by discharging the excessive mist M early, excessive penetration of hydrogen peroxide into the inner surface of the bottle B can be prevented.

Before the bottle B is fed to the air rinsing step, the bottle B with the mist M of hydrogen peroxide solution introduced therein is desirably left alone for a predetermined time in order to improve the sterilization effect. However, as described above, the inner surface of the bottle B has been modified by the corona discharge treatment, and a uniform coating of hydrogen peroxide solution is quickly formed. Thus, the process can proceed to the air rinsing step immediately after the introduction of hydrogen peroxide solution. Thus, the time for the sterilization process can be reduced. In addition, thermal deformation of the bottle B can be avoided by lowering the temperature of the air.

Instead of the air rinsing process with the bottle B being held in the upright position shown in FIG. 8(C1), an air rinsing process with the bottle B being held in the inverted position as shown in FIG. 9(G2) may be adopted. If the process shown in FIG. 9(G2) is adopted, and the aseptic air N is blasted into the bottle B in the inverted position through the opening part p3 facing down, foreign matters or the like in the bottle B are more likely to drop to the outside of the bottle B. Alternatively, following the air rinsing step shown in FIG. 8(G1), the step shown in FIG. 9(G2) may be performed without blasting the aseptic air N.

Although the aseptic air is blasted into the bottle B from the nozzle 50 disposed outside of the bottle B in the air rinsing step, the nozzle 50 may be inserted into the bottle B to blast the aseptic air N into the bottle B. As in the preliminary heating step, the nozzle 50 is desirably inserted to the bottle diameter transition region.

After the air rinsing, as shown in FIG. 9(H), the bottle B is fed to a water rinsing step.

In the water rinsing step, the bottle B is inverted, a nozzle 51 is inserted into the bottle B, and heated aseptic warm water W as a cleaner is fed into the bottle B from the nozzle 51. The aseptic water may be at room temperature. By injecting the warm water W into the bottle B, the hydrogen peroxide on the inner surface of the bottle B is rinsed out of the bottle B. Foreign matters are also removed. As in the preliminary heating step and the air rinsing step, the nozzle 51 is desirably inserted into the bottle B to the bottle diameter transition region.

As described above, as a result of the corona discharge treatment on the preform P, a uniform thin coating of a small amount of hydrogen peroxide solution is deposited on the inner surface of the bottle B. Thus, the remaining hydrogen peroxide can be satisfactorily removed only in the air rinsing step. If the remaining hydrogen peroxide is already satisfactorily removed, the water rinsing step described above can be omitted.

In addition, since the bottle B is sterilized before the bottle B is molded from the preform P, the steps shown in FIGS. 8(E) to 9(H) can be omitted.

After the predetermined sterilization process described above is performed, as shown in FIG. 9(I), the bottle B is filled with a drink "a" from a nozzle 52. The drink "a" is sterilized in advance.

As shown in FIG. 9(J), the bottle B filled with the drink "a" is sealed by screwing the cap C onto the opening part p3 of the bottle B. The cap C is sterilized in advance.

Although not shown, a conveyor device including a wheel chain or the like for conveying the preform P or bottle B is provided in the path along which the preform P is subjected to the preform preliminary heating step (FIG. 7(A)) and molded into the bottle B and then the bottle B is subjected to the sealing step (FIG. 9(J)). In addition, at least the path from the hydrogen peroxide solution supply step for the preform P (FIG. 7(B)) to the sealing step for the bottle B (FIG. 9(J)) is covered with an aseptic chamber. Thus, filling of the bottle with the content is aseptically and automatically performed.

Second Embodiment

According to a second embodiment, a conductor that differs in structure from the conductor according to the first embodiment is used for the corona discharge treatment.

Figure 6:
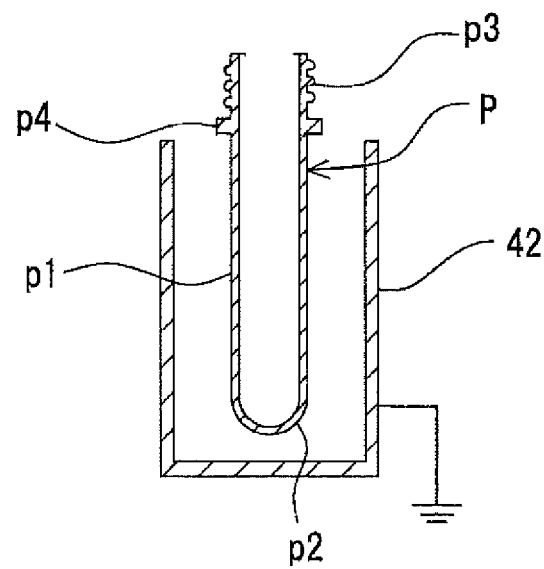
FIG. 6 is a schematic diagram showing a modification of a conductor grounded.

As shown in FIG. 6, a grounding part 42 (which is an example of a conductor grounded) includes no insulating part and is formed only by a conductor grounded.

In this case, the preform P is set in such a manner that the preform P is not in contact with the conductive grounding part 42. In addition, the opening part p3 of the preform P slightly protrudes beyond the opening part of the grounding part 42.

Third Embodiment

First, a configuration and general functions of an apparatus that performs a corona discharge treatment on a bottle, which is a kind of container made of resin, will be described with reference to FIGS. 11, 12 and 3.

Figure 11:
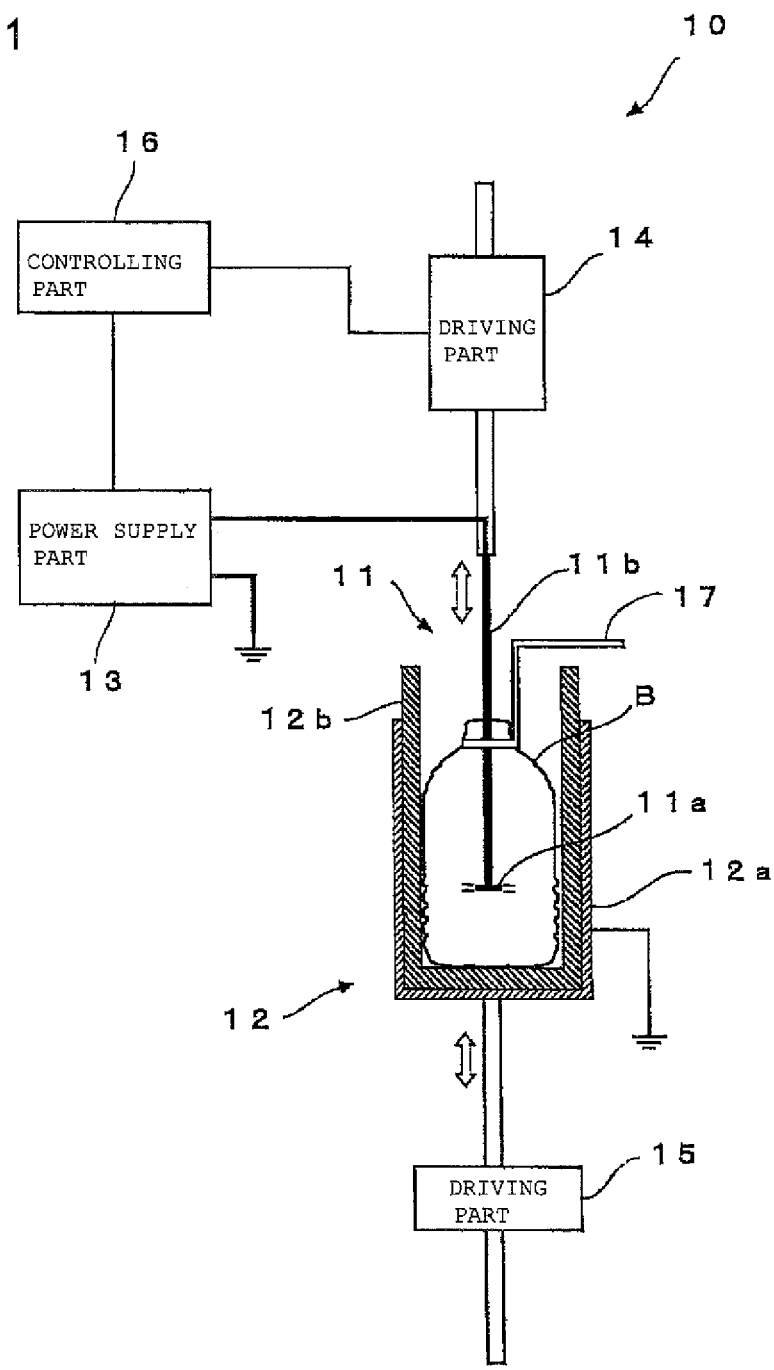
FIG. 11 is a schematic diagram showing an example of an apparatus for performing a corona discharge treatment on a container made of resin.

As shown in FIG. 11, a corona discharge treatment apparatus 10 includes an electrode 11 that can pass through an opening part of a bottle B, which is a container made of resin, a grounding part 12 that is grounded, a power supply part 13 that applies to the electrode 11 a voltage produced in a corona discharge, a driving part 14 that inserts the electrode 11 into the bottle B, a driving part 15 that drives the grounding part 12 to cover the bottle B, and a controlling part 16 that controls operation of the driving parts 14 and 15.

The corona discharge treatment apparatus 10 modifies an inner surface of the bottle B with a corona discharge. For example, electrons emitted from the electrode 11 in a corona discharge are accelerated in the electrical field and collide with electrons or molecules in the air to cause excitation, dissociation or ionization of atoms or molecules. The ionized atoms or molecules also emit electrons. Upon reaching a surface layer of a resin, electrons cleave main or side chains of the polymer. The surface layer of the polymer in which main and side chains are cleaved are chemically radical. When oxygen radicals, ozone molecules or the like in the gas phase are combined with the main or side chains, polar functional groups, such as hydroxyl groups or carbonyl groups, are introduced to impart hydrophilicity to the surface layer of the resin, thereby improving the wettability. In this way, the surface of the resin is modified.

The bottle B is held at a predetermined position in the corona discharge treatment apparatus 10 by a holding part 17.

Figure 12:
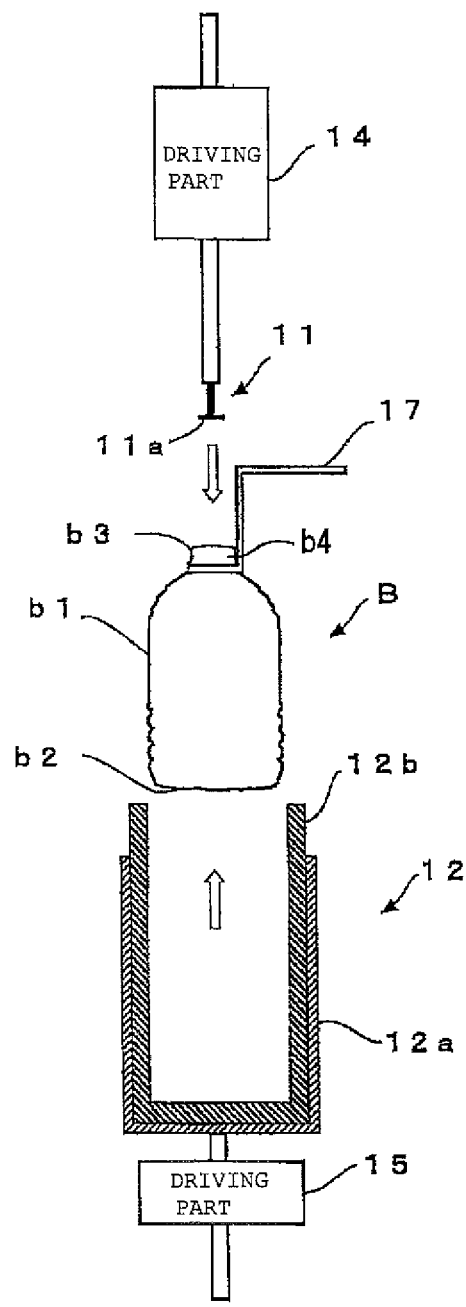
FIG. 12 is a schematic diagram showing an example of the apparatus shown in FIG. 11 in which the container made of resin is set.

As shown in FIG. 12, the bottle B has a trunk part b1, a bottom part b2 that closes the bottom of the trunk part b1, and at least one opening part b3 provided opposite to the bottom part b2.

The trunk part b1 of the bottle B has a substantially cylindrical shape, for example. The trunk part b1 is widened from the opening part b3 and transitions to the cylindrical shape. To increase the strength of the bottle B, the trunk part b1 of the bottle B may partially have a corrugated wall extending in the direction from the bottom part b2 to the opening part b3. The trunk part b1 of the bottle B may have another shape, such as a square cylindrical shape.

The opening part b3 has a tubular shape and has a male thread formed on the outer side. As shown in FIG. 21(F), a female thread of a cap C can be engaged with the female thread of the opening part b3. The bottle B is closed by the engagement of the male and female threads. The size of the opening in the opening part b3 is smaller than the size of the bottom part b2 and smaller than the cross section of the trunk part b1. In addition, a flange-shaped support ring b4 is formed on the outer side of the opening part b3. The bottle B is suspended by the holding part 17 with the support ring b4 hooked on the holding part 17.

The bottle B is made of a polyolefin, such as low density polyethylene, high density polyethylene, linear low density polyethylene, polypropylene or cyclic polyolefin, or a mixture of two or more of these polyolefins, or a non-olefin resin, such as ethylene-vinylalcohol copolymer, nylon or polyethylene terephthalate, and is formed by a single layer or two or more layers of any of these resins. At least the inner surface of the bottle B is made of any of the resins described above. The bottle B may have a volume of 500 mL, for example.

The substance to fill the bottle B is not limited to liquid but can contain particles, granules or the like or can be a viscous substance.

The electrode 11 has the same structure as the electrode shown in FIG. 3 and has an electrode discharge part 11a and an electrode post 11b.

The electrode 11 is a conductor made of metal, such as stainless steel. The electrode 11 has a shape and size that allows the electrode 11 to pass through the opening part of the bottle B and has a length that allows the electrode 11 to come close to the inner surface of the bottom part of the bottle B. For example, the electrode discharge part 11a has a disk-like shape and has a diameter smaller than the inner diameter of the opening part b3 of the bottle B, and the electrode post 11b has a length that allows the electrode discharge part 11a to come close to the inner surface of the bottom part of the bottle B.

The grounding part 12 (which is an example of a conductor grounded) has a conductive part 12a, which is a conductor made of metal such as stainless steel, and an insulating part 12b, which is made of resin or the like. Examples of the conductor include stainless steel, iron, copper, brass, aluminum, a gold-plated metal, carbon, or a conductive polymer.

The conductive part 12a (which is an example of a grounded conductor provided around at least a part of the outside of the bottle) has a bottom part and is shaped to cover the bottom part b2 and the trunk part b1 of the bottle B. For example, if the trunk part b1 of the bottle B has a cylindrical shape, the conductive part 12a also has a cylindrical shape but is larger than the bottle B. The conductive part 12a is grounded.

The insulating part 12b (which is an example of an insulator between the bottle and the conductor) is made of resin and has a predetermined thickness. The insulating part 12b is located between the bottle B and the conductive part 12a and serves as a spacer. For example, the insulating part 12b has a bottom part and is shaped on the inner side to receive the bottle B and on the outer side to be housed in the conductive part 12a. The insulating part 12b is in contact with the conductive part 12a at a part of the circumferential surface thereof and at the bottom part thereof.

Examples of the material of the insulating part 12b include a phenol resin, an epoxy resin, polypropylene, polyethylene, or polyethylene terephthalate.

The insulating part 12b protrudes beyond the conductive part 12a in the direction of the opening of the bottle B. In other words, the length (depth) of the insulating part 12b in the lengthwise direction is greater than the height of the bottle B.

The length (depth) of the conductive part 12a in the lengthwise direction is preferably approximately equal to the height of the opening part b3 of the bottle B in the state where the insulating part 12b exists.

The power supply part 13 is a power supply that generates a high voltage at a constant voltage, a constant current or a constant power. The power supply part 13 has a converter that performs frequency conversion to raise the frequency of the commercial power supply, a high-voltage transformer that boosts the voltage to the voltage of the corona discharge, and the like. The power supply part 13 applies a high voltage produced in the corona discharge to the electrode 11.

The driving part 14 (which is an example of a driving device) has a motor, such as a servo motor. The driving part 14 is coupled to the electrode 11. As shown in FIG. 12, the driving part 14 performs a driving operation to insert the electrode 11 into the bottle B through the opening part of the bottle B. The driving part 14 then performs a driving operation to bring the electrode 11 close to the inner surface of the bottom part of the bottle B and then withdraw the electrode 11 from the bottle B. The driving part 14 may rotate the electrode 11 about an axis of the electrode 11 in the lengthwise direction (the direction of the opening of the bottle B) while inserting or withdrawing the electrode 11 into or from the bottle B.

The driving part 15 (which is an example of a driving device) has a motor, such as a servo motor. The driving part 15 is coupled to the bottom part of the grounding part 12. As shown in FIG. 2, the driving part 15 drives the grounding part 12 to cover the bottle B from the bottom thereof. After a discharge treatment, the driving part 15 drives the grounding part 12 to remove the grounding part 12 from around the bottle B. The driving part 15 may rotate the grounding part 12 with the bottle B set therein about the axis of the electrode 11 in the lengthwise direction (the direction of the opening of the bottle B) along with the bottle B.

The controlling part 16 has a central processing unit (CPU) and a memory. The CPU controls turn on/off, voltage or the like of the power supply part 13 according to a program stored in the memory and controls driving operations of the driving parts 14 and 15. The controlling part 16 can also control operation of the holding part 17.

Next, a surface treatment on the bottle B by the corona discharge treatment apparatus 10 will be described with reference to FIGS. 13 to 14E.

Figure 13:
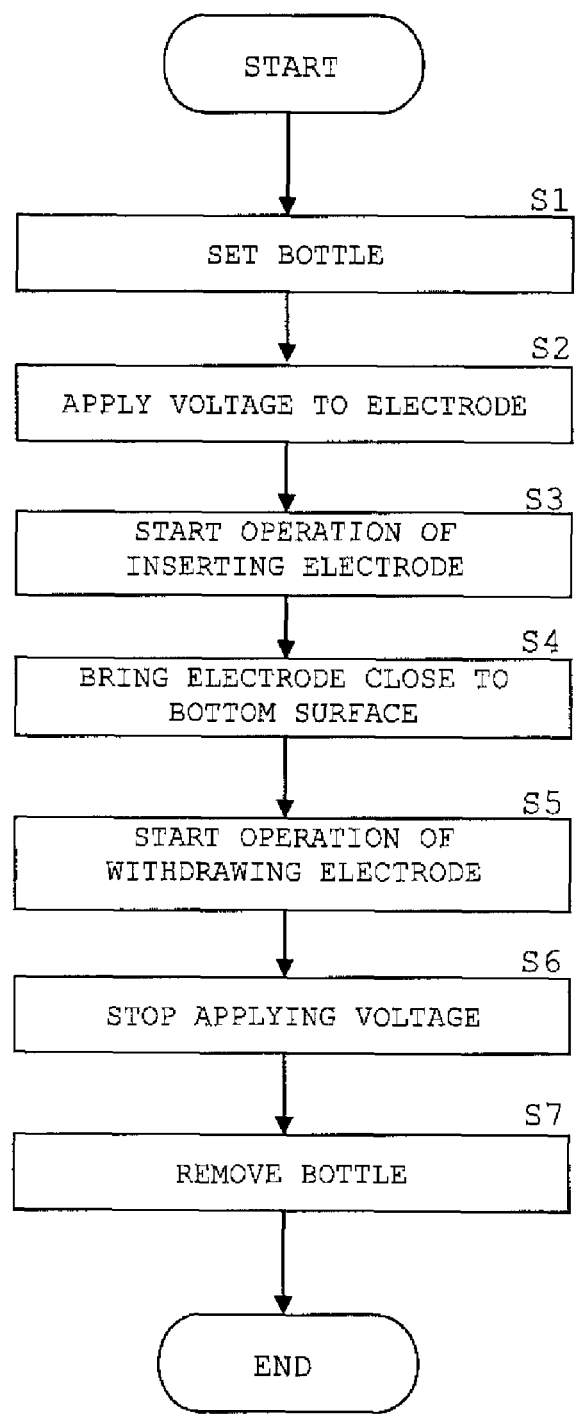
FIG. 13 is a flowchart showing an example of an operation of the apparatus shown in FIG. 11.

As shown in FIG. 13, the bottle B is set in the corona discharge treatment apparatus 10 (Step S1). More specifically, a conveyor (not shown) for the bottle B conveys the blow-molded bottle B to the corona discharge treatment apparatus 10.

As shown in FIG. 12, the bottle B held by the holding part 17 is set at a predetermined position in the corona discharge treatment apparatus 10. The corona discharge treatment apparatus 10 checks whether the bottle B is set at the predetermined position, using a sensor or the like.

Figure 14A:
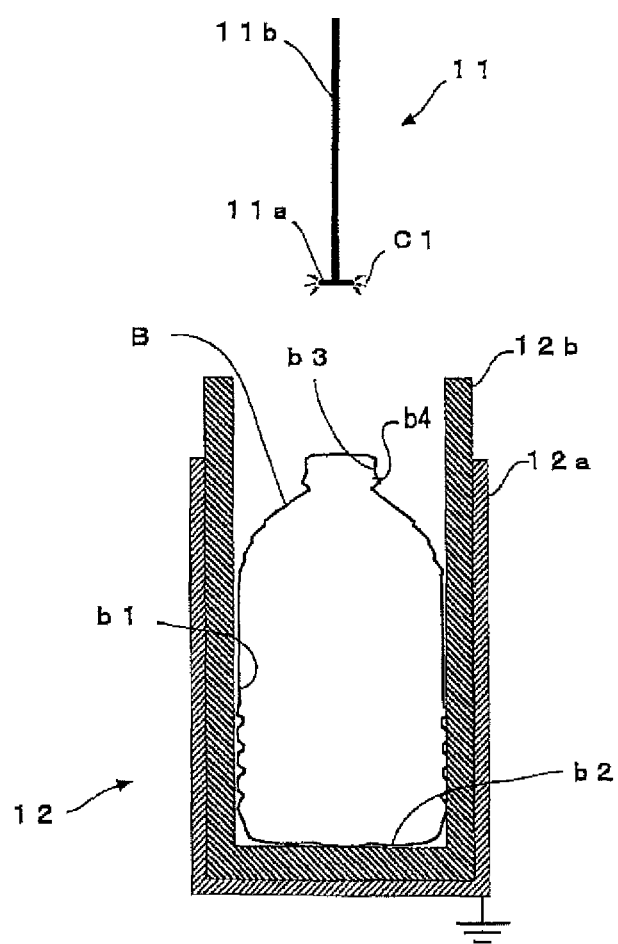
FIG. 14A is a schematic diagram showing how a corona discharge treatment is performed in the apparatus shown in FIG. 11.

Under the control of the controlling part 16 of the corona discharge treatment apparatus 10, the driving part 15 then drives the grounding part 12 in the direction of the opening of the bottle B so that the bottle B is housed in the grounding part 12 from the bottom part of the bottle B. As shown in FIG. 14A, the bottle B is thus housed in the grounding part 12. At this point in time, the bottle B is held by the holding part 17, although not shown.

The corona discharge treatment apparatus 10 then applies a voltage to the electrode 11 (Step S2).

More specifically, under the control of the controlling part 16 of the corona discharge treatment apparatus 10, the power supply part 13 applies a voltage to the electrode 11 so that the electrode discharge part 11a of the electrode 11 produces a corona discharge in the air. As shown in FIG. 14A, a corona discharge C1 occurs at a circumferential part of the disk of the electrode discharge part 11a. Since the electrode discharge part 11a is spaced apart from the conductive part 12a of the grounding part 12, the corona discharge C1 is in a discharge mode of low directivity.

The corona discharge treatment apparatus 10 then starts an operation of insertion of the electrode 11 (Step S3).

More specifically, under the control of the controlling part 16, the driving part 14 for the electrode 11 starts an operation of insertion of the electrode 11 producing a corona discharge. The driving part 14 may rotate the electrode 11 during the insertion. Alternatively, the driving part 15 may rotate the grounding part 12 along with the bottle B so that the bottle B and the electrode 11 rotate with respect to each other.

Figure 14B:
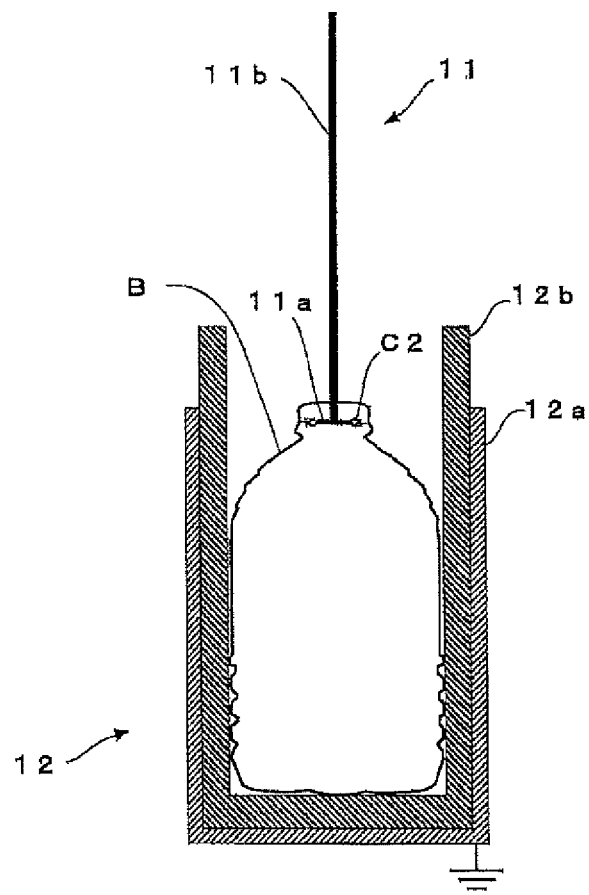
FIG. 14B is a schematic diagram showing how a corona discharge treatment is performed in the apparatus shown in FIG. 11.

As the electrode discharge part 11a comes closer to the conductive part 12a, the corona discharge changes to a discharge mode with higher directivity to the conductive part 12a. As shown in FIG. 14B, when the electrode discharge part 11a enters the opening part b3 of the bottle B, the corona discharge occurring at the circumferential part of the electrode discharge part 11a changes to a corona discharge C2 in a discharge mode of higher directivity. The corona discharge C2 is in a discharge mode of high directivity. As the electrode discharge part 11a passes through the narrower interior of the opening part b3 of the bottle B, the surface of the interior of the opening part b3 is modified by the corona discharge C2.

The surface of the interior of the opening part b3 of the bottle B and the circumferential part of the electrode discharge part 11a are close to each other. Thus, the driving part 14 may quickly pass the electrode discharge part 11a through the interior of the opening part b3.

Figure 14C:
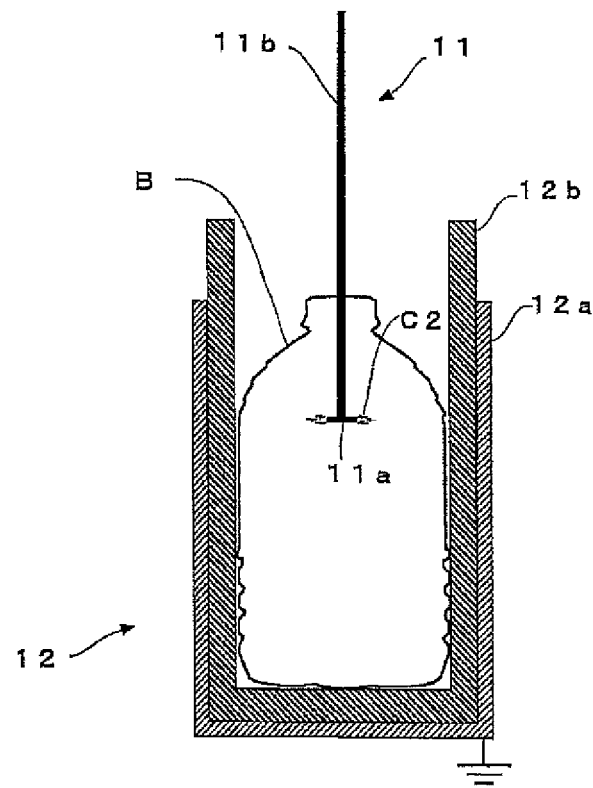
FIG. 14C is a schematic diagram showing how a corona discharge treatment is performed in the apparatus shown in FIG. 11.

As shown in FIG. 14C, the driving part 14 further inserts the electrode 11 into the bottle B. As the electrode 11 is inserted deeper into the bottle B, the inner surface of the trunk part b1 of the bottle B is modified by the corona discharge C2.

The corona discharge treatment apparatus 10 then bring the electrode 11 close to the bottom surface of the bottle B to treat the inner surface of the bottom part b2 of the bottle B (Step S4).

More specifically, under the control of the controlling part 16, the driving part 14 for the electrode 11 brings the electrode discharge part 11a close to the inner surface of the bottom part b2 of the bottle B.

Figure 14D:
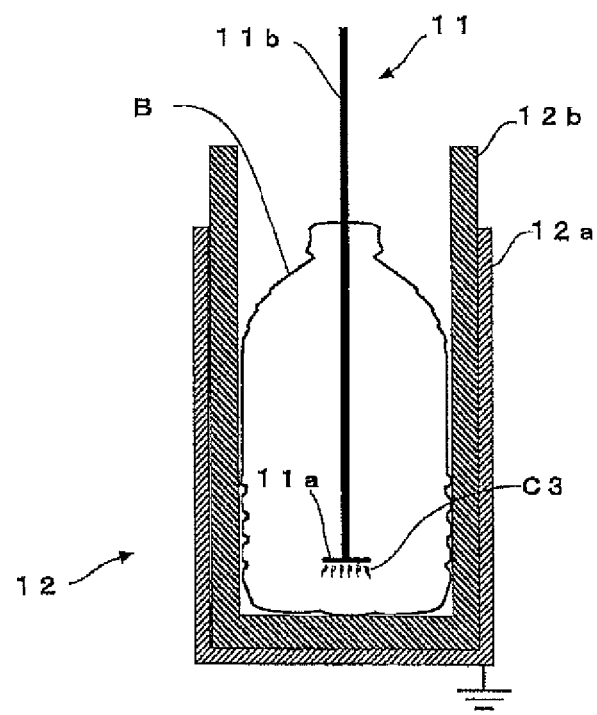
FIG. 14D is a schematic diagram showing how a corona discharge treatment is performed in the apparatus shown in FIG. 11.

As shown in FIG. 14D, when the electrode discharge part 11a comes close to the inner surface of the bottom part b2 of the bottle B, a corona discharge C3, which is a surface discharge, occurs at a circular surface part (a surface opposed to the bottom surface of the conductive part 12a) of the electrode discharge part 11a. The corona discharge C3 (which is an example of a discharge for treatment of the inner surface of the bottom part b2 of the bottle B), which is a surface discharge, occurs at the surface part of the electrode discharge part 11a because the impedance between the surface part of the electrode discharge part 11a and the conductive part 12a of the grounding part 12 is lower than the impedance between the circumferential part of the electrode discharge part 11a and the conductive part 12a of the grounding part 12. In other words, the corona discharge changes the discharge mode from the corona discharge C2 to the corona discharge C3.

The inner surface of the bottom part b2 of the bottle B starts being modified by the corona discharge C3, which is a surface discharge.

The driving part 14 or 15 may rotate the electrode 11 and the bottle B with respect to each other about the axis in the direction of the opening of the bottle B while bringing the electrode 11 close to the inner surface of the bottom part b2 of the bottle B.

Figure 14E:
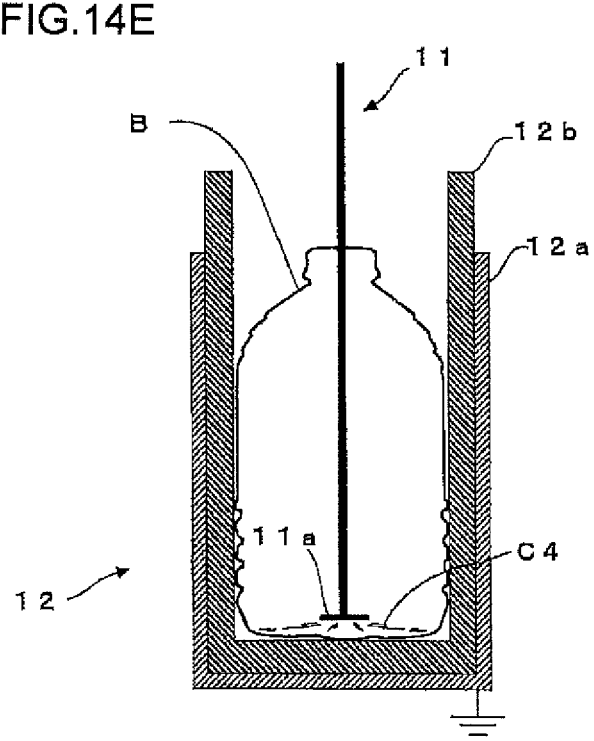
FIG. 14E is a schematic diagram showing how a corona discharge treatment is performed in the apparatus shown in FIG. 11.

As the electrode discharge part 11a comes closer to the inner surface of the bottom part b2 of the bottle B, as shown in FIG. 14E, the corona discharge changes the discharge mode from the corona discharge C3 to a discharge C4 (which is an example of the discharge for treatment of the inner surface of the bottom part b2 of the bottle B). The discharge C4 is a surface discharge that occurs along the inner surface of the bottom part b2. The discharge is the corona discharge that is produced from the surface part of the electrode discharge part 11a and spreads over the entire inner surface of the bottom part b2 along the inner surface of the bottom part b2 of the bottle B. The discharge C4 facilitates modification of the entire inner surface of the bottom part b2.

The corona discharge treatment apparatus 10 then starts an operation of withdrawing the electrode 11 (Step S5). More specifically, under the control of the controlling part 16, the driving part 14 for the electrode 11 starts the operation of withdrawing the electrode 11 producing the corona discharge. As the electrode 11 is withdrawn, the discharge mode changes from the discharge C4 to the corona discharge C3 and then from the corona discharge C3 to the corona discharge C2. The inner surface of the bottle B is also modified during the operation of withdrawing the electrode 11. The driving part 14 may rotate the electrode 11 while withdrawing the electrode 11. Alternatively, application of the voltage can be stopped when the operation of withdrawing the electrode 11 is performed.

The corona discharge treatment apparatus 10 then stops application of the voltage (Step S6).

More specifically, under the control of the controlling part 16, the power supply part 13 stops applying the voltage to the electrode 11 to stop production of the corona discharge when the electrode 11 is positioned again as shown in FIG. 14A.

The interior of the opening part b3 of the bottle B is closer to the circumferential part of the electrode discharge part 11a and is more readily modified. Thus, the power supply part 13 can stop applying the voltage to the electrode 11 when the electrode 11 is positioned as shown in FIG. 14B.

The corona discharge treatment apparatus 10 removes the bottle B (Step S7).

Under the control of the controlling part 16, the driving part 14 drives the grounding part 12 so that the bottle B is removed from the grounding part 12. The bottle B held by the holding part 17 is removed from the predetermined position in the corona discharge treatment apparatus 10, and the bottle B is then conveyed by a conveyor to a position for the subsequent step.

As described above, according to this embodiment, the electrode 11 having passed through the opening part b3 of the bottle B is brought close to the inner surface of the bottom part b2 of the bottle B, and the mode of the corona discharge is changed so that the bottom part b2 of the bottle B can also be efficiently treated. Thus, the whole of the interior of the bottle B can be efficiently modified. In addition, the corona discharge can be produced in the normal air, and a special gas such as argon does not need to be supplied, so that the cost can be reduced.

If the electrode 11 is brought closer to the inner surface of the bottom part b2 of the bottle B until the discharge C4 occurs along the inner surface of the bottom part b2 of the bottle B, the entire inner surface of the bottom part b2 is more readily modified. In addition, the bottom part b2 is modified in a shorter time.

If there is the grounded conductive part 12a (which is an example of the conductor) around at least part of the outside of the bottle B, the directivity of the discharge from the electrode discharge part 11a to the bottle B is improved, and the inner surface of the bottle B can be more efficiently modified.

If there is the insulating part 12b (which is an example of the insulator) between the bottle B and the conductive part 12a, the discharge from the electrode discharge part 11a is stabilized, and uniform modification is facilitated.

If the insulating part 12b (which is an example of the insulator) protrudes beyond the conductive part 12a (which is an example of the conductor) in the direction of the opening of the bottle B, a stable discharge from the electrode 11 is ensured over the entire inner surface of the bottle B including the top of the opening part b3 of the bottle B, so that appropriate surface treatment can be achieved.

If the electrode 11 and the bottle B are rotated with respect to each other about the axis in the direction of the opening of the bottle B when the electrode 11 is brought close to the inner surface of the bottom part b2 of the bottle B, the surface treatment can be more uniformly achieved.

By the corona discharge treatment described above, the inner surface of the bottle B is modified to have higher wettability. More specifically, the inner surface modified by the corona discharge treatment has a contact angle with water of approximately 75 degrees or less, whereas the inner surface yet to be modified has a contact angle with water of approximately 98 degrees, for example.

The bottle B whose inner surface has been modified by the corona discharge treatment as described above is subjected to a sterilization process described below.

First, as shown in FIG. 20(A), the bottle B is subjected to a preliminary heating step, in which a nozzle 43 is inserted into the bottle B through the opening part b3 of the bottle B. Heated air is fed into the bottle B from the nozzle 43.

In the preliminary heating, nozzles 44, 44 are installed to be opposed to the outer surface of the opening part b3 of the bottle B, and heated air is blasted from the nozzles 44, 44 to the opening part b3 to further heat the opening part b3. This is because the opening part b3 and the support ring p4 are relatively thick and cannot be sufficiently heated only by the heated air from the nozzle 43.

The nozzle 43 is inserted into the bottle B in order to ensure that the heated air be fed into the bottle B. The extent to which the nozzle 43 is inserted can be appropriately changed depending on the flowrate of the heated air, the diameter of the opening part b3 or the like. However, as shown in FIG. 20(A), the tip end of the nozzle 43 is preferably located in the bottle diameter transition region between the opening part b3 and the trunk part b1 of the bottle B. The transition region can be defined as a region from the lower end of the opening part b3 to a level at which the diameter of the bottle is 70% of the maximum diameter of the bottle, for example. The preliminary heating is desirably performed until the temperature of the inner surface of the bottle B becomes 40° C. or higher.

The container preliminary heating described above is performed as required, and can be omitted.

The preliminarily heated bottle B is conveyed for a hydrogen peroxide supply step.

In the hydrogen peroxide supply step, as shown in FIG. 20(B), the mist M or gas G of hydrogen peroxide solution or mixture thereof is supplied into the bottle B from the nozzle 45.

The mist M or gas G of hydrogen peroxide solution or mixture thereof is produced by a producer 46 having the same structure as that shown in FIG. 10, for example. The hydrogen peroxide solution is an aqueous solution containing 20% by weight to 60% by weight of hydrogen peroxide and also contains an additive, such as a stabilizer. The concentration of hydrogen peroxide is preferably 35% by weight.

The producer 46 includes a hydrogen peroxide solution supplying part 47 that serves as a twin fluid sprayer that atomizes the aqueous solution of hydrogen peroxide serving as a sterilizer and supplies the resulting spray, and an evaporating part 48 that evaporates the spray of hydrogen peroxide solution supplied from the hydrogen peroxide solution supplying part 47 by heating the spray to a temperature equal to or higher than the boiling point of the hydrogen peroxide solution and equal to or lower than the non-degradable temperature thereof. The hydrogen peroxide solution supplying part 47 is configured to receive hydrogen peroxide solution and compressed air through a hydrogen peroxide solution supply channel 47a and a compressed air supply channel 47b, respectively, and spray the hydrogen peroxide solution into the evaporating part 48. The evaporating part 48 is a pipe with a heater 48a interposed between an inner wall and an outer wall thereof, and heats and evaporates the spray of hydrogen peroxide solution blasted into the pipe. The gas G of hydrogen peroxide solution resulting from the evaporation is ejected to the opening of the opening part b3 of the bottle 1 from a nozzle 45 in the form of the mist M or gas G or mixture thereof.

As shown in FIG. 20(B), some of the mist M or gas G or mixture thereof ejected from the nozzle 45 enters the bottle B through the opening part b3, and some flows down on the exterior of the bottle B.

Thus, the fine mist M of hydrogen peroxide solution is deposited on the inner and outer surfaces of the bottle B. As described above, the inner surface of the bottle B is modified by the corona discharge treatment. Thus, when the mist M is deposited on the inner surface of the bottle B, in particular, the hydrogen peroxide solution is spread to form a uniform thin coating on the entire inner surface of the bottle B. Thus, nonuniform sterilization is prevented, and the sterilization effect is improved.

If the bottle B is heated in the preliminary heating described above, not only the inner surface but also the outer surface of the bottle B is effectively sterilized by the hydrogen peroxide.

The amount of deposition of the mist of hydrogen peroxide solution per bottle with a volume of 500 mL preferably ranges from 5 μL to 100 μL of a 35%-by-weight hydrogen peroxide solution. That is, the amount of the mist M is preferably set so that the same amount of hydrogen peroxide as the hydrogen peroxide contained in 5 μL to 100 μL of a hydrogen peroxide solution containing 35% by weight of hydrogen peroxide is deposited on the interior of the bottle B. The duration of the blasting of the mist M preferably ranges from 0.1 seconds to 1 second per bottle.

As shown in FIG. 20(B), a tunnel 49 through which the bottle B passes is provided below the nozzle 45, as required.

Since the tunnel 49 is filled with the mist M of hydrogen peroxide solution, the mist M of hydrogen peroxide solution is more readily deposited on the outer surface of the bottle B, and the effect of sterilization of the outer surface of the bottle B is improved accordingly.

As shown in FIG. 20(C1), the bottle B is subjected to an air rinsing step.

The air rinsing step is performed by blasting aseptic air N into the bottle B from a nozzle 50. The hydrogen peroxide, foreign matter and the like are removed from the bottle B by the flow of the aseptic air N.

Although the aseptic air N is desirably hot air obtained by heating air, the aseptic air N may be at room temperature. If the hot air is blasted into the bottle B, the interior of the bottle B is heated, and the sterilization effect of the mist M of hydrogen peroxide solution is improved, and penetration of the hydrogen peroxide into the surface of the bottle B is suppressed and the hydrogen peroxide is likely to remain on the inner surface of the bottle B. In addition, the mist floating in the bottle B is discharged by the hot air to the outside of the bottle B. At this point in time, sterilization has been sufficiently achieved by the mist M of hydrogen peroxide solution deposited on the inner surface of the bottle B, and thus, the sterilization effect is not compromised by discharging the mist M floating in the inner space of the bottle B. Rather, by discharging the excessive mist M early, excessive penetration of hydrogen peroxide into the inner surface of the bottle B can be prevented.

Before the bottle B is fed to the air rinsing step, the bottle B with the mist M of hydrogen peroxide solution introduced therein is desirably left alone for a predetermined time in order to improve the sterilization effect. However, as described above, the inner surface of the bottle B has been modified by the corona discharge treatment, and a uniform coating of hydrogen peroxide solution is quickly formed. Thus, the process can proceed to the air rinsing step immediately after the introduction of hydrogen peroxide solution. Thus, the time for the sterilization process can be reduced. In addition, thermal deformation of the bottle B can be avoided by lowering the temperature of the air.

Instead of the air rinsing process with the bottle B being held in the upright position shown in FIG. 20(C1), an air rinsing process with the bottle B being held in the inverted position as shown in FIG. 20(C2) may be adopted. If the process shown in FIG. 20(C2) is adopted, and the aseptic air N is blasted into the bottle B in the inverted position through the opening part b3 facing down, foreign matters or the like in the bottle B are more likely to drop to the outside of the bottle B. Alternatively, following the air rinsing step shown in FIG. 20(C1), the step shown in FIG. 20(C2) may be performed without blasting the aseptic air N.

Although the aseptic air is blasted into the bottle B from the nozzle 50 disposed outside of the bottle B in the air rinsing step, the nozzle 50 may be inserted into the bottle B to blast the aseptic air N into the bottle B. As in the preliminary heating step, the nozzle 50 is desirably inserted to the bottle diameter transition region.

After the air rinsing, as shown in FIG. 20(D), the bottle B is fed to a water rinsing step.

In the water rinsing step, the bottle B is inverted, a nozzle 51 is inserted into the bottle B, and heated aseptic warm water H as a cleaner is fed into the bottle B from the nozzle 51. The aseptic water may be at room temperature. By injecting the warm water H into the bottle B, the hydrogen peroxide on the inner surface of the bottle B is rinsed out of the bottle B. Foreign matters are also removed. As in the preliminary heating step and the air rinsing step, the nozzle 51 is desirably inserted into the bottle B to the bottle diameter transition region.

As described above, as a result of the corona discharge treatment on the bottle B, a uniform thin coating of a small amount of hydrogen peroxide solution is deposited on the inner surface of the bottle B. Thus, the remaining hydrogen peroxide can be satisfactorily removed only in the air rinsing step. If the remaining hydrogen peroxide is already satisfactorily removed, the water rinsing step described above can be omitted.

After the predetermined sterilization process described above is performed, as shown in FIG. 21(E), the bottle B is filled with a drink "a" from a nozzle 52. The drink "a" is sterilized in advance.

As shown in FIG. 21(F), the bottle B filled with the drink "a" is sealed by screwing the cap C onto the opening part b3 of the bottle B. The cap C is sterilized in advance.

Although not shown, a conveyor device including a wheel chain or the like for conveying the bottle B is provided in the path along which the bottle B is fed from the preliminary heating step (FIG. 20(A)) to the sealing step (FIG. 20(F)). In addition, at least the path from the hydrogen peroxide solution supply step (FIG. 20(B)) to the sealing step (FIG. 21(F)) is covered with an aseptic chamber. Thus, filling of the bottle with the content is aseptically and automatically performed.

Example

The sterilization process was performed under various conditions for cases where the corona discharge treatment was performed and where the corona discharge treatment was not performed. The result is shown in Table 1.

In this example, bottles having a volume of 500 mL made of high density polyethylene and ethylene-vinylalcohol copolymer as an intermediate layer were produced by multilayer blow molding. The contact angle with water of the inner surface of the bottle that was not subjected to the corona discharge treatment was 98°. On the other hand, the contact angle with water of the inner surface of the bottle that was subjected to the corona discharge treatment was 63°.

TABLE 1

| | HYDROGEN PEROXIDE STERILIZATION | | | | AIR RINSING | | STERILIZATION EFFECT | |
|---|---|---|---|---|---|---|---|---|
| CONDI-TION | TEMPER-ATURE (° C.) | DURATION (SECOND) | AMOUNT (g/min) | GAS CONCEN-TRATION (mg/L) | TEMPER-ATURE (° C.) | CORONA DISCHARGE TREATMENT | INNER SURFACE OF OPENING PART | INNER SURFACE OF TRUNK PART |
| A | 115 | 4.2 | 9.5 | 8.1 | 115 | PERFORMED | >6.1 | >6.1 |
| | | | | | | NOT | 5.8 | >6.1 |

TABLE 1-continued

| | HYDROGEN PEROXIDE STERILIZATION | | | | | | STERILIZATION EFFECT | |
|---|---|---|---|---|---|---|---|---|
| | | | | GAS | AIR RINSING | | | |
| CONDI-TION | TEMPER-ATURE (° C.) | DURATION (SECOND) | AMOUNT (g/min) | CONCEN-TRATION (mg/L) | TEMPER-ATURE (° C.) | CORONA DISCHARGE TREATMENT | INNER SURFACE OF OPENING PART | INNER SURFACE OF TRUNK PART |
| B | 115 | 3.7 | 9.5 | 8.1 | 115 | PERFORMED | >6.1 | 6.1 |
| | | | | | | NOT PERFORMED | 5.1 | 5.7 |
| C | 115 | 3.2 | 9.5 | 8.1 | 115 | PERFORMED | >6.1 | >6.1 |
| | | | | | | NOT PERFORMED | 5.1 | 5.6 |
| D | 115 | 3.2 | 7.5 | 6.4 | 115 | PERFORMED | >6.1 | >6.1 |
| | | | | | | NOT PERFORMED | 3.9 | 4.2 |
| E | 115 | 3.2 | 5.5 | 4.7 | 115 | PERFORMED | >6.1 | >6.1 |
| | | | | | | NOT PERFORMED | 3.5 | 3.9 |

The sterilization effect in Table 1 was calculated according to the following formula for *Bacillus atrophaeus* as an indicator organism, which was grown in a SCD broth culture for 8 days at 35° C. A higher value indicates a higher sterilization effect.

Sterilization effect=Log(number of inoculated bacteria/number of bacteria after sterilization)

The number of bacteria after sterilization was the most probable number statistically calculated from numbers of bacteria for a plurality of sterilized samples.

The sterilization effect is sufficiently high if the value is higher than 6. It can be seen that the duration of supply of hydrogen peroxide is reduced when the corona discharge treatment is performed, and sufficient sterilization effect is achieved even if the amount of supply of hydrogen peroxide is reduced. It can also be seen that practical sterilization effect cannot be achieved if the amount of supply of hydrogen peroxide is reduced when the corona discharge treatment is not performed.

Fourth Embodiment

According to a fourth embodiment, the corona discharge treatment is performed by using various modifications of the electrode.

First, various modifications of the shape of the electrode will be described with reference to FIGS. 15(A) to 15(E).

As shown in FIG. 15(A), an electrode 21 that can pass through the opening part b3 of the bottle B made of resin has an electrode post 21b and three or more bar-shaped electrode discharge parts 21a that extends radially.

In this case, the corona discharges C1 and C2 occur at the tip ends of the bar-shaped electrode discharge parts 21a. The corona discharge C3 and the discharge C4 occur on the side surface of the bar-shaped electrode discharge parts 21a toward the bottom b2 of the bottle B.

As shown in FIG. 15(B), an electrode 22 that can pass through the opening part b3 of the bottle B made of resin has a T-shape formed by an electrode post 22b and a bar-shaped electrode discharge part 22a extending in opposite directions from the tip end of the electrode post 22b.

As shown in FIG. 15(C), an electrode 23 that can pass through the opening part b3 of the bottle B made of resin has an L-shape formed by an electrode post 23b and a bar-shaped electrode discharge part 23a extending in one direction from the tip end of the electrode post 23b.

As shown in FIG. 15(D), an electrode 24 that can pass through the opening part b3 of the bottle B made of resin has a rounded L-shape formed by a bar-shaped electrode post 23b, a curved electrode part 24c and an electrode discharge part 24a.

As shown in FIG. 15(E), an electrode 25 that can pass through the opening part b3 of the bottle B made of resin has a gently curved shape formed by an electrode post 25b and an electrode discharge part 25a.

In order to achieve as uniform modification as possible, any of the electrodes 21, 22, 23, 24 and 25 shown in FIGS. 15(A) to 15(E) is preferably rotated about the axis in the direction of the opening of the bottle B with respect to the bottle B when the respective electrode is brought close to the inner surface of the bottom part b2 of the bottle B.

Next, the operation of inserting the electrode 24 into the bottle B will be described with reference to FIGS. 16(A) to 16(E).

In FIGS. 7(A) to 7(E), illustration of the grounding part 12 is omitted.

As shown in FIG. 16(A), in Step S3, the tip end of the electrode discharge part 24a of the electrode 24, to which a voltage has been applied in Step S2, is inserted by the driving part 14 into the opening part b3 of the bottle B. In this step, the driving part 14 is rotating the bottle B.

As shown in FIG. 16(B), the driving part 14 then adjusts the orientation of the electrode 24 until the electrode post 24b becomes parallel to the direction of the opening of the bottle B, while passing the tip end of the electrode discharge part 24a through the opening part b3 of the bottle B. The inner surface of the opening part b3 and the expanding part connecting to the trunk part b1 of the bottle B is modified.

As shown in FIGS. 16(C) and 16(D), once the electrode post 24b becomes parallel to the direction of the opening of the bottle B, the driving part 14 drives the electrode 24 along the direction of the opening of the bottle B to bring the electrode discharge part 24a close to the inner surface of the bottom part b2 of the bottle B while modifying the inner surface of the trunk part b1 of the bottle B with the corona discharge C2.

As shown in FIG. 16(E), in Step S4, the driving part 14 then brings the electrode discharge part 24a close to the inner surface of the bottom part b2 of the bottle B until the discharge mode changes. The corona discharge C3 occurs on the side surface (the surface opposed to the bottom surface of the conductive part) of the electrode discharge part 24a. Since the electrode 24 and the bottle B are rotating with respect to each other, the whole of the inner surface of the bottom part b2 of the bottle B is likely to be modified.

Fifth Embodiment

According to a fifth embodiment, an expandable electrode whose tip end can be opened and closed is used for the corona discharge treatment.

Figure 17A:
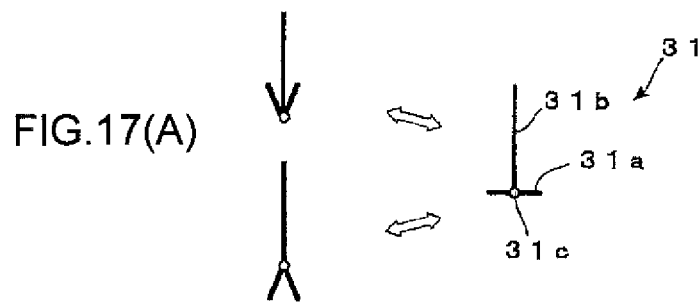
FIGS. 17(A) to 17(C) are schematic diagrams showing expandable electrodes that are modifications of the electrode shown in FIG. 1.

As shown in FIG. 17(A), an electrode 31 may have a bar-shaped electrode post 31b, two bar-shaped electrode discharge parts 31a, and a hinge part 31c at which the electrode discharge parts 31a are expanded. The electrode discharge parts 31a are opened and closed about the hinge part 31c.

Figure 17B:
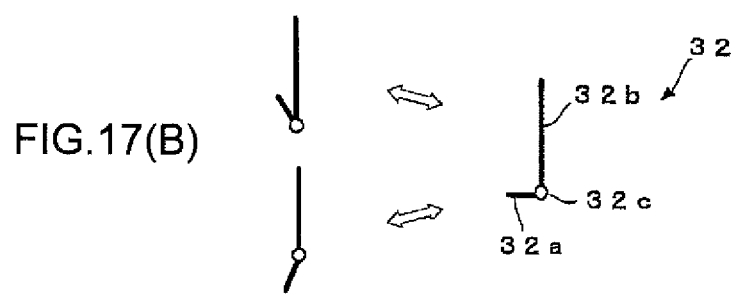

As shown in FIG. 17(B), an electrode 32 may have a bar-shaped electrode post 32b, one bar-shaped electrode discharge part 32a, and a hinge part 32c at which the electrode discharge part 32a is expanded.

Figure 17C:
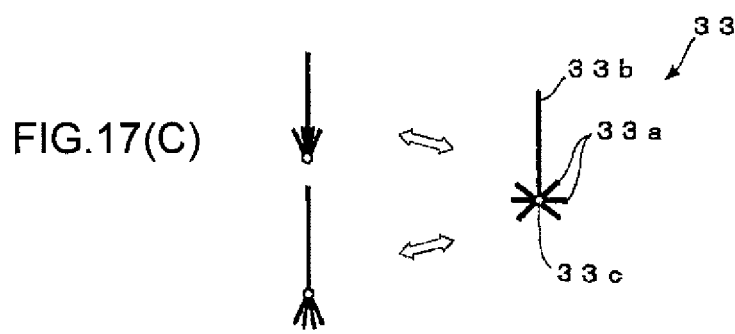

As shown in FIG. 17(C), an electrode 33 may have a bar-shaped electrode post 33b, three or more bar-shaped electrode discharge parts 33a arranged in an umbrella-like configuration, and a hinge part 33c at which the electrode discharge parts 33a are expanded.

When the electrode discharge part(s) 31a, 32a, 33a passes through the opening part b3 of the bottle B, the driving part 14 closes the electrode discharge part(s) 31a, 32a, 33a so that the electrode discharge part(s) can pass through the opening part b3. The electrode discharge part(s) can be closed by folding the electrode discharge part(s) 31a, 32a, 33a back onto the electrode post 31b, 32b, 33b or by folding the electrode discharge part(s) 31a, 32a, 33a in front of the electrode post 31b, 32b, 33b.

The hinge part 31c, 32c, 33c (which is an example of an expansion mechanism that allows the electrode to be expanded after the electrode discharge part(s) passes through the opening part b3 of the bottle B) has a mechanism that allows the electrode discharge part(s) to rotate about the hinge part 31c, 32c, 33c. For example, a mechanism that pulls the electrode discharge part(s) by wire, a mechanism that allows the electrode discharge part(s) 31a, 32a, 33a to open under their own weight, a spring mechanism, and a mechanism similar to an umbrella folding mechanism are possible.

The discharging electrode 31, 32, 33 passes through the narrow opening part b3 of the bottle B while rotating about the electrode post 31b, 32b, 33b. After the electrode discharge part(s) 31a, 32a, 33a have passed through the opening part b3, the electrode 31, 32, 33 is expanded by opening the electrode discharge part(s) 31a, 32a, 33a. After the electrode discharge part(s) 31a, 32a, 33a is opened, the driving part 14 drives the electrode 31, 32, 33 to move to the bottom part b2 of the bottle B while rotating the electrode 31, 32, 33 about the electrode post 31b, 32b, 33b.

Figures 18A, 18B, 18C:
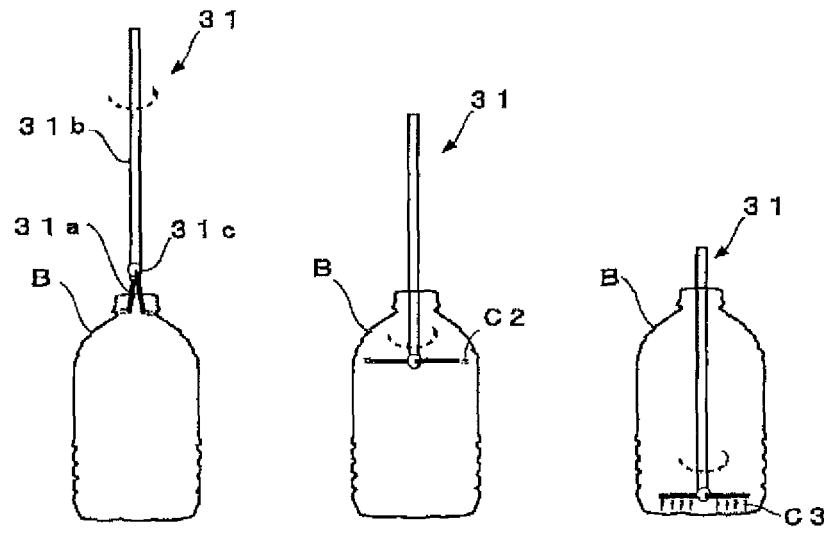
FIGS. 18(A) to 18(C) are schematic diagrams showing how a corona discharge treatment is performed by the electrode shown in FIG. 17(A).

In the case of the electrode 31, as shown in FIG. 18(A), in Step S3, the electrode discharge parts 31a that are closed pass through the narrow opening part b3 of the bottle B while rotating about the electrode post 31b. The corona discharge from the tip end of the electrode discharge parts 31a modifies the inner portion of the opening part b3. The electrode discharge parts 31a may be slightly opened to come closer to the inner surface of the tubular opening part b3.

As shown in FIG. 18(B), the electrode discharge parts 31a producing the corona discharge at the tip end thereof starts being opened along the inner circumference of the bottle B from the opening part b3 to the trunk part b1, while rotating. When the electrode 31 reaches a position where the trunk part b1 has the maximum inner diameter, the electrode discharge parts 31a are fully opened. The corona discharge from the tip end of the electrode discharge parts 31a modifies the inner portion of the trunk part b1. If the trunk part b1 is constricted, the electrode discharge parts 31a may be slightly closed at the constriction.

As shown in FIG. 18(C), in Step S4, when the opened electrode discharge parts 31a come close to the bottom part b2, a corona discharge occurs on the bar-shaped electrode discharge parts 31a. The corona discharge from the rotating electrode discharge parts 31a modifies the inner surface of the bottom part b2 of the bottle B.

If the electrode 31, 32, 33 has the expansion mechanism that allows the electrode to be expanded after the electrode discharge part(s) passes through the opening part b3 of the bottle B, after the electrode discharge part(s) passes through the opening part b3 of the bottle B, the tip end (electrode discharge part(s) 31a, 32a, 33a) of the electrode is opened, and the electrode discharge part(s) 31a, 32a, 33a come close to the inner surface of the side wall part (the inner side of the opening part b3 and the inner part of the trunk part b1) of the bottle B. Thus, the inner surface of the side wall part of the bottle B can be efficiently modified.

In FIGS. 18(A) to 18(C), illustration of the grounding part 12 is omitted.

Sixth Embodiment

According to a sixth embodiment, a conductor that differs in structure from the conductor according to the third embodiment is used for the corona discharge treatment.

Figure 19:
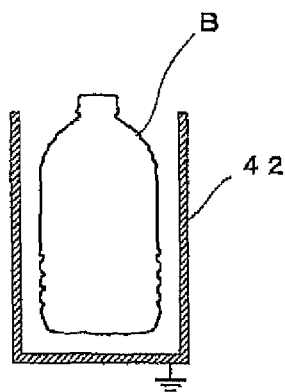
FIG. 19 is a schematic diagram showing a modification of the conductor grounded.

As shown in FIG. 19, the grounding part 42 (which is an example of the conductor grounded) has no insulating part and is formed only by a conductor grounded.

In this case, the bottle is set in such a manner that the bottle B is not in contact with the conductive grounding part 42. In addition, the opening part b3 of the bottle B slightly protrudes beyond the opening part of the grounding part 42.

Although the present invention is configured as described above, the present invention is not limited to the embodiments described above. The embodiments described above are given only for illustrative purposes, and any concept that provides substantially the same configurations, as well as effects and advantages, as the technical concept described in the claims is included in the technical scope of the present invention.

Although the present invention is configured as described above, the present invention is not limited to the embodiments described above. The embodiments described above are given only for illustrative purposes, and any concept that provides substantially the same configurations, as well as effects and advantages, as the technical concept described in the claims is included in the technical scope of the present invention. For example, although a bottle is used as a target of the corona discharge treatment and the sterilization process in the embodiments described above, the application of the present invention is not limited to the bottle, and the present invention can be applied to any containers made of resin that have other shapes, such as a cup or a tray.

REFERENCE SIGNS LIST 10 corona discharge treatment apparatus
11, 21, 22, 23, 24, 25, 31, 32, 33 electrode 11a, 21a, 22a, 23a, 24a, 25a, 31a, 32a, 33a electrode discharge part
12, 42 grounding part (an example of a conductor grounded)
12a conductive part (an example of a conductor grounded)
12b insulating part
13 power supply part
14, 15 driving part (driving device)
16 controlling part
B bottle
b2 bottom part
b3 opening part
C1, C2, C3 corona discharge
C4 discharge
P preform
p1 trunk part
p2 bottom part
p3 opening part
p4 support ring

The invention claimed is:

1. A method of sterilizing a preform, wherein a sterilization process is performed on a preform that is made primarily of polyethylene terephthalate after a corona discharge treatment is performed on an inner surface of the preform, the corona discharge treatment including a voltage application step of applying a voltage produced in a corona discharge to an electrode that is capable of passing through an opening part of the preform, an insertion step of inserting the electrode to which the voltage is applied into the preform through the opening part, and a bottom part treatment step of treating an inner surface of a bottom part of the preform by bringing the electrode close to the bottom part until the corona discharge from the electrode changes discharge mode, and the sterilization process including a hydrogen peroxide supplying step of blasting a mist or gas of hydrogen peroxide solution or a mixture thereof to the preform.

2. The method of sterilizing a preform according to claim 1, wherein the corona discharge treatment is performed with a grounded conductor being provided around at least a part of the outside of the preform.

3. The method of sterilizing a preform according to claim 2, wherein the corona discharge treatment is performed with an insulator being provided between the preform and the conductor.

4. The method of sterilizing a preform according to claim 3, wherein the corona discharge treatment is performed with the insulator protruding beyond the conductor in a direction toward the opening part of the preform.

5. The method of sterilizing a preform according to claim 1, wherein the corona discharge treatment is performed by bringing the electrode close to the inner surface of the bottom part of the preform while rotating the electrode and the preform with respect to each other about a central axis in the direction toward the opening part of the preform.

6. The method of sterilizing a preform according to claim 1, wherein the corona discharge treatment is performed so that a contact angle with water of the surface of the preform is equal to or less than 75 degrees.

7. The method of sterilizing a preform according to claim 1, wherein the mist or gas of hydrogen peroxide or mixture thereof is blasted to the preform after the preform is preliminarily heated by blasting heated air into the preform and blasting heated air to a thick part of the preform from outside of the preform.

8. The method of sterilizing a preform according to claim 1, wherein the mist or gas of hydrogen peroxide or mixture thereof is produced by injecting a hydrogen peroxide solution and aseptic air into an evaporator from a twin fluid nozzle.

9. A method of sterilizing a container made of resin, wherein a sterilization process is performed on a container made of resin after a corona discharge treatment is performed on an inner surface of the container made of resin, the corona discharge treatment including a voltage application step of applying a voltage produced in a corona discharge to an electrode that is capable of passing through an opening part of the container made of resin, an insertion step of inserting the electrode to which the voltage is applied into the container made of resin through the opening part, and a bottom part treatment step of treating an inner surface of a bottom part of the container made of resin by bringing the electrode close to the bottom part until the corona discharge from the electrode changes discharge mode, and the sterilization process including a hydrogen peroxide supplying step of blasting a mist or gas of hydrogen peroxide solution or a mixture thereof to the container made of resin.

10. The method of sterilizing a container made of resin according to claim 9, wherein the opening part of the container made of resin is narrow, and the corona discharge treatment is performed on the inner surface of the container made of resin by an electrode that is expanded after the electrode enters the container made of resin through the opening part.

11. The method of sterilizing a container made of resin according to claim 9, wherein the corona discharge treatment is performed with a grounded conductor being provided around at least a part of the outside of the container made of resin.

12. The method of sterilizing a container made of resin according to claim 11, wherein the corona discharge treatment is performed with an insulator being provided between the container made of resin and the conductor.

13. The method of sterilizing a container made of resin according to claim 12, wherein the corona discharge treatment is performed with the insulator protruding beyond the conductor in a direction toward the opening part of the container made of resin.

14. The method of sterilizing a container made of resin according to claim 9, wherein the corona discharge treatment is performed by bringing the electrode close to the inner surface of the bottom part of the container made of resin while rotating the electrode and the container made of resin with respect to each other about a central axis in the direction toward the opening part of the container made of resin.

15. The method of sterilizing a container made of resin according to claim 9, wherein at least the inner surface of the container made of resin is made of polyolefin or polyethylene terephthalate.

16. The method of sterilizing a container made of resin according to claim 9, wherein the corona discharge treatment is performed so that a contact angle with water of the surface of the container made of resin is equal to or less than 75 degrees.

17. The method of sterilizing a container made of resin according to claim 9, wherein the mist or gas of hydrogen peroxide or mixture thereof is blasted to the container made of resin after the container made of resin is preliminarily heated by blasting heated air into the container made of resin and blasting heated air to a thick part of the container made of resin from outside of the container made of resin.

18. The method of sterilizing a container made of resin according to claim 9, wherein the mist or gas of hydrogen peroxide or mixture thereof is produced by injecting a hydrogen peroxide solution and aseptic air into an evaporator from a twin fluid nozzle.

19. The method of sterilizing a container made of resin according to claim 9, wherein the sterilization process includes an air rinsing step performed after the hydrogen peroxide supplying step.

20. The method of sterilizing a container made of resin according to claim 9, wherein the sterilization process includes a water rinsing step performed after the hydrogen peroxide supplying step.

* * * * *